United States Patent [19]

Lereclus

[11] Patent Number: 5,766,586
[45] Date of Patent: Jun. 16, 1998

[54] GRAM-POSITIVE BACTERIA REPLICON

[75] Inventor: Didier Lereclus, Paris, France

[73] Assignees: Institut Pasteur; Institut National de la Recherche Agronomique, both of Paris Cedex, France

[21] Appl. No.: 178,242

[22] PCT Filed: Jun. 20, 1992

[86] PCT No.: PCT/FR92/00711

§ 371 Date: May 18, 1994

§ 102(e) Date: May 18, 1994

[87] PCT Pub. No.: WO93/02199

PCT Pub. Date: Feb. 4, 1993

[30] Foreign Application Priority Data

Jul. 22, 1991 [FR] France ................................. 91 09240

[51] Int. Cl.$^6$ .......................... A01N 63/00; C12N 1/21; C12N 15/31; C12N 15/63
[52] U.S. Cl. ...................... 424/93.461; 424/93.4; 424/93.46; 424/93.462; 435/320.1; 435/252.3; 435/252.31; 536/23.1; 536/23.7; 536/23.71; 536/24.1
[58] Field of Search .................. 435/320.1, 252.3, 435/252.31; 536/23.1, 23.7, 23.71, 24.1; 424/93.4, 93.46, 93.461, 93.462

[56] References Cited

PUBLICATIONS

Lereclus et al, FEMS Microbiology Letters, 1989, vol. 60: pp. 211–218.

Lereclus et al, FEMS Microbiology Letters, 1988, vol. 49: pp. 417–422.

*Primary Examiner*—George C. Elliott
*Assistant Examiner*—Terry A. McKelvey
*Attorney, Agent, or Firm*—Oblon, Spivak, McClelland, Maier & Neustadt, P.C.

[57] ABSTRACT

A recombinant vector capable of replicating in Gram positive bacteria and containing: a) a nucleotide concatenation I of Bacillus thuringiensis with a size of about 2.6 kb between sites BalI-HpaI, or any fragment included in said concatenation as long as its allows replication of the recombinant vector when under the control of functional promoter in Gram positive bacteria, or any sequence which hybridizes with the complementary sequence of concatenation I or the above mentioned fragment under highly stringent conditions, and b) at least on DNA sequence of interest inserted in phase with the above mentioned concatenation.

74 Claims, 18 Drawing Sheets

```
CCATCCTCCAAAGTTGGAGAGTGAGTTTATGTCCCAAATATTAAGTTTCTGGTGAACCTTATCAAATTTCGTTGATTTAATAGAAACATAGCGGTA
1                                                                                    -35
AAATTAGCAGTAACTTAATAGAACGGAAATGAAAAAGCCACTCTCATATGCTATTGGCTACCAACCTTTAGCGAGAATGACTTAATCCTGTACAGCCA
100 -10
TACAGGACTTCGACTTATAAGAGGCGCCAACCTCAAATAAGTTATTTGCCTTGTTTCCGAACAAGGCTTATTAGATACACCTATGTACCGTTACTC
200
TACGAATATTTCAACTAGTAATTACTACCATTGTCTCATATACATAATAAAAGGCCGTTTTCTATACCTAGAAGTCTTGTAAATGTACAG
300
GGCGTTTAGATATAGAGAACGCCCTTTTTTGTGTTCCGTTCAACTGTCTGACGTAAGCCAGGTAAGACACAAGCCTTGCATAAAACAAGCCTACGGATGTAAATCCTAATAAT
400
CGGATATCAGTTGTCGTTGCATTCAACTGTCTGACGTAAGCCAGGTAAGACACAAGCCTTGCATAAAACAAGCCTACGGATGTAAATCCTAATAAT
500
GATGATAACCAAGACGTTAGCGGCAAAAAGTGTTGGGGGTTCAAATAAGACATGTGCGACTGAGTTAAACAGTTACTCCTAAGCGCGATCAT
600
GACACTGATTCACGGCTATTCTTGTACAAGCTTTATTACAAGGATATATGCGGGTTATATAGCGAATCACCCGAAAGGGAACGGTGTGGGCGTGAGAAAC
700
GCACCCGTACGGCGCAATACAATGCCAATAAGCTATATACGGGTATGAGTAGTAGTTTTGTAACCTCGTAAATTTCAACAGGGTTACTATGCCCAAAACTACACCTTCAGATTCCT
800
CGAGACCTCGGCATCAAGCCATACGAATGAGTGGCCGTTTAAGACCTTAAGTCAAGGATTTGAAGGATTTGAAGGATTTAACCTCGTAATATGCCCAAAACTACACCTTCAGATTCCT
900
AACAAACTCGCCAGTATGAAGGAAATGGCTAGACAAGGCAGAGAATCCAGAGTCGTTTAAATCAAGTGAAAGACAAGATGAAATTAAAAGAATAGTGAAAGATAGGGAC
1000
CCATTAACTAAGATAGTGGGGATTGAGGAAGAACAAGGCAGGGTTTATTGATCTATTGTAGACTTTATGGTAAAGAATCCTCATTTATTTGTTAAT
1100
TGGTTCTCTATGAAGGAAATGGCTAGACAAGGCAGAGAATCCAGAGTCGTTTATTGATCTATTGTAGACTTTATGGTAAAGAATCCTCATTTATTTGTTAAT
1200
```

FIG.1A-1

```
GGTACAGAGGATGAAAGTAATAATGTTGTTACAAAATGTAATAGTGATATTAAAGAGGTTGCCGAGTCATATTTAACTCTTTTATAGTGAGAGGTTAA
                    .                    .                    .                    .
                  1300
AACTAATTAATATGTATTAAGGCCCAATGTTGGAATTATTGTATTTCACTAGGCAACCTACTTACTAAAAGTAAGATTATCCATTAGTGGATGTTATAA
                    .                    .                    .                    .
                  1400
TATTGGTTTTTAACACAATAATCATCGGCTTTCCGTCGTCGTTTGATAGAAAAGTAACCATTAGCGATGAGAAAAAGTCAATATAAAAAGCCATCCGTAA
                    .                    .                    .                    .
                  1500
AAAACGGATGGCTTACCGTACATAGGATCGTTGGTAGGGCCGTATCCTACATCTCTGGTAACTTACCTAGCCAATCAAATGCTTGAGAACGGCGGTT
                    .                    .                    .                    .
                  1600
AGATAAGCGCGTGGGAACCTTTCCCACCTCAAAGATCCTATATCATTATTATGTTACTTTCTACAGGTAGTATACCATGTTCTTATATTTAGTAAAC
                    .                    .                    .                    .
                  1700
TCCCCGTTAGCTTAACAGGTCTCTTGTAAGCAATTAAAACGTCCACTATTCAATCGTCTTGGATTTTCCAGGACCGTTTTTAGATCGAACATAGTTGA
                    .                    .                    .                    .
                  1800
   ***SerLeuLeuAspLysTyrAlaIleLeuArgArgGlySerAsnLeuArgArgGlnIleLysAlaProGlyAsnLeuAspPheMetThrSer
TAAGAACAAATAACCCGCTTGGGTCCAACTTTATAGCAATTAGTATATGGTCATTTAAAATCTTTACCAATTCAACCCTATTAGGTTCTTCTTAGGATTTG
                    .                    .                    .                    .
                  1900
LeuPheLeuTyrGlySerProAspLeuLysIleAlaIleLeuIleHisAspAsnLeuIleLeuValSerAsnProGluValProGlnLysProAsnGln
CCCGACATAGTCGGGGTCTTCAACGATATCTTTATGCGATGAATATTTTCATAAATACCAGCAGTGTCTTCTTTCTTCTGCTGCTTTATAAATCCCGC
                    .                    .                    .                    .
                  2000
GlyValTyrAspProHisGluValIleValIleAspLysIleTyrIleGlyTyrLysGluTyrIleGlnLysLysValHisLysIleLysPheGlyPro
AAACATTTTTACATCGTTAGAAGTGCAAGTCAAGTTATATGATTTGTGGAAGTTTTGCCACAACAGTGGTTTATTTACAATCTTTT
                    .                    .                    .                    .
                  2100
PheMetLysValAspAsnSerThrCysThrLeuAsnTyrThrAspIleIleIleGlnProLeuLysAlaValValThrProLysAsnValIleLysLys
TTTATTAGCCGTCAAATTTCTCCCTCATCTCGTCTCTTTATATCTTTATTTATCATAAAGGAGTATTGAACCGTCGCGGCGGGACAGGTTTATGATAG
                    .                    .                    .                    .
                  2200
LysAsnAlaThrMet start orf1
```

FIG. 1A-2

```
GGATATTTTATTGAATAATTGATGGTATAAGGGACTTTCATGCTTGGAAAGTGGGGATTATGAATTAGATGCTTGTCCACAATATGTTCCAATGTAATT
    .      .      2300      .      .      .      .      -10      .      .      -35.
AAAATTTATGTTCCCACCTTGACCAAACATCACGTCCATACTTAAATCGTCCCTCCTTTAATAGGTAAAATATTAATTTACCTTAATAAAAAAATAATG
    .      .   -35 2400      .      .-10      .      .      .      .      .
                              start orf2  MetLeuGlyIleLeuPheThrAlaAlaProSerThrAspValValLysAspLeu
GATAATAGTATTCGTCTGAATTTATATAATCAGGGGAACTATTGATGCTGGGGATACTATTTACAGCGGCGCCATCTACTGATGTCGTAAAGGATTTG
    .      .      2500      .      .      .      .      .      .      .
GlnAspLysValIleSerLeuGlnAspHisGluValAlaPheLeuAsnThrThrIleSerAsnMetLeuThrAlaValGlyIleGlyValAlaIleIle
CAAGATAAAGTTATATCATTGCAGGATCATGAGGTAGCGTTTTTGAACACCACGATATCTAATATGTTAACAGCAGTAGGTATTGGAGTGGCAATTATA
    .      .      2600      .      .      .      .      .      .      .
ThrAlaValPheThrAlaAlaPheAlaTyrValThrTyrSerAsnLysArgAlaLysLysAsnMetAspGluAlaSerArgLysLeuGluGluAlaGlu
ACGGCGGTTTTTACAGCAGCGTTTGCTTATGTTACATATTCTAATAAGCGTGCTAAAAAGAATATGGACGAGGCTAGTAGAAAATTAGAAGAAGCAGAA
    .      .      2700      .      .      .      .      .      .      .
SerLysValSerValLeuGluGluLysSerAlaGlnLeuGluArgLysIleLeuGluAlaGluGlnLeuLeuAlaAspAlaAsnSerIleSerAsnVal
AGTAAAGTTTCTGTGCTAGAGGAGAAAAGCGCTCAATTGGAGAGGAAGATTCTTGAAGCTGAACAACTCTTAGCTGATGCCAATTCTATTTCTAATGTGG
    .      .      2800      .      .      .      .      .      .      .
```

```
     CCATCCCTCCAAAGTTGGAGAGTGAGTTTTATGTCGCAAATATTAATGTTTCTGGTGAACC
 61  TTATCAAATTTCGTTGATTTAATAGAAACATAGCGGGTAAAATTAGCAGTAACTTAATAG
                    -35                                    -10
121  AACGGAAATGAAAAAGCCACTCTCATATGCTATTGGCTACCAACCTTTAGCGAGAATGA
181  CTAATCCTGTACAGCCATACAGGACTTCGACTTATAAGAGGCGCCAACCTCAAATAAGT
241  TATTTGCCTTGTTTCGCGAACAAGGCTTATTAGATACACCTATTGTACCGTTACTCTAC
301  GAATATTTCAACTAGTAATTACTAGCATTGTCATATACATAATAAACGGATATAAAAGG
361  GCGTTTTCTATACCTAGAAGTCTTGTAAATGTACAGGGCGTTAGATATAGAGAACGCCC
421  TTTTGTGTTCCGTTCCAGTGGAAGCTACCACTTTAAAAGATGGTCTAGTGTAGCCAAT
481  GCAGGAGAGTACACTCGGATATCAGTGTCGTTGCATTCAACTGTCTGACGTAAGCGAGG
541  TAAAGGACACAAGCCTTGCATAAAACAAGCCTACGGGATGTAAATCCTAATAATGATGAT
601  AACCAAGAGCGTTAGCGGCAAAAGTGTTGGGGGTTCAAAATAAGACATGATTGTGCGACT
661  GGAGTTAAACAGTTACTCGTAAGCGGCGATCATGACACTGATTCACGGCTATTCTTGTAC
721  AAGCTTTATTACAAGGATATGCGGGTTATATAGCGAATCACCCGAAAGGGAACGGTGTTG
```

```
 781
      GGCGTGAGAAACGCACCGTACGGGCGCAATACAATGCCAATAAGCTATATACGGACGGTAT
 841
      AGTAGTTTTGTAAGCTATAACCGTTTGTCGTCAATGCAACCAATCTCAATTCGAGACCTC
 901
      GGCATCTAAGCCAGTACGAATGAGTGGGCCGTTTAACCTCGTAAATTTCAACAGGGGTT
 961
      ACTATGCCCAAAACTACATTCAGATTCCTAACAAACTCGCCAGTATGAAAACCTTAAGA
1021
      CCTTAAAGTCAAGGGATTTGAAGGATTTAACCTCGATTAGCAAAAAATGTAGAGTACTG
1081
      AAGCAACTACCATTAACTAAGATAGTGGGGATTGAGGAAGAATCCAGAGCTGGTTCTCTATG
1141
      CAAGTGAAAGACAAGCTAGAGAACAAAGGCAGCGGTTTATTGATCTATTGTTAGACTTTATG
1201
      AGAAAGGAAATGCTAGAGAACAAGGATGAAAGTAATAATGTTGTTACA
1261
      GTAAAGAATCCTCATTTATTTGTTAATGGTACAGAGGTTGCGGAGTCATATTTAACTCTTTTATAGTGAGAG
1321
      AAATGTAATAATAGTGATATTAAAGAGGTTGCGGAGTCATATTTAACTCTTTTATAGTGAGAG
1381
      GGTTAAAACTAATTAATATGTATTAAGGCCCAATGTTGGAATTATTGTATTCACTAGGC
```

FIG. 1B-2

1441 AACCTACTTACTAAAAGTAAGATTATCCATTAGTGGATGTTATAATATTGGGTTTTTAA
1501 CACAATAATCATCGCCTTTCGGTGTCGTTTGATAGAAAAGTAACCATTAGCGATGAAAAA
1561 GTCAATATAAAAGCCATCCGTAAAAAACGGATGGCTTACCGTACATAGGATCGTTGGTA
1621 GGGGGGGCGTATCCTACATCTCTGGTAACTTACCTAGCCAATCAAATGCTTGAGAACGGCG
1681 GTTAGATAAGCCGCTGGGGAACCTTCCCACCTCAAAGATCCTATATCATTATTATGTTA
1741 CTTTCTACAGGTAGTATACCATGTTCTTATATTTAGTAAACTCCCGTTAGCTTAACAG
1801 GTCTTTGTAAGCAATTAACGTCCACTATTCAATCGTCTTTGGATTTTCCAGGACCGTT
1861 TTTAGATCGAACATAGTTGATAAGAACAAATAACCGCTTGGGTCCAACTTTATAGCAAT
1921 TAGTATATGGTCATTTAAAATCTTTACCAATTCAACGCTATTAGGTTCTTTAGGATTTTG
1981 CCCGACATAGTCGGGTGTTCAACGATATCTTTATGTGCGATGAATATTTTCATAAAT
2041 ACCAGGATGTTGTTTCTTTACGTGCTTTATAAATCCGGGAAACATTTTTACATCGTTAGA
2101 AGTGCAAGTCAAGTTATATGTATCTATAATGATTGTGGAAGTTTGCCACAACAGTTGG
2161 TTTATTTACAATCTTTTTTTTATTAGCCGTCAAATTCTCCCTCATCTCGTCTCTTATA

FIG. 1B-3

2221 TCTTTATTTTATCATAAAGGAGTATTTGAACCGTCGCGCGGGGACACAGGTTTATGATAGGA
2281 TATTTTATTGAATAATTGATGGTATAAGGGACTTTCATGCTTGGAAAGTGGGATTATGA
2341 ATTAGATGCTTGTCCCACAATATGTTCCAATGTAATTAAAATTTATGTTCCCACCTTGACC
2401 AAACATCACGTCCATACTTAAATCGTCCCTCCCTTTAATAGGTAAAATATTAATTACCTT
2461 AATAAAAAAATAATGGATAATAGTATTCGTCTGAATTTATATAATCAGGGGAACTATTG
2521 ATGCTGGGGATACTATTTACAGCGGCGCCATCGAGGTAGCGTTTTTGAACACCACGATGTCGTAAAGGATTTGCAAGAT
2581 AAAGTTATATCATTGCAGGATCATGAGGTAGCGTTTTTTACAGCAGCGTTTGCT
2641 TTAACAGCAGTAGGTATTGGAGTGGCAATTATAACGGACGAGGCTAGTAGAAAATTA
2701 TATGTTACATATTCTAATAAGCGTGCTAAAAAGAATATGGACGAGGCTAGTAGAAAATTA
2761 GAAGAAGCAGAGAAAGTAAAGTTTCTGTGCTAGAGGAGAAAGCGCTCAATTGGAGAGGAAG
2821 ATTCTTGAAGCTGAACAACTCTTAGCTGATGCCCAATTCTATTTCTAATGTGG

FIG. 1B-4

MetThrAlaAsnLysLysLysIleValAsnLysProThrValValAlaAlaLysLeuPro

GlnIleIleIleAspThrTyrAsnLeuThrCysThrSerAsnAspValLysMetPhe

ProGlyPheIleLysHisValLysLysGlnHisProGlyIleTyrGluLysTyrSer

SerHisIleLysAspIleValGluHisProAspTyrValGlyGlnAsnProLysGlu

ProAsnSerValGluLeuValLysIleLeuAsnAspHisIleLeuIleAlaIleLys

LeuAspProSerGlyTyrLeuPheLeuSerThrMetPheAspLeuLysAsnGlyPro

AlaLysIleGlnArgArgLeuAsnSerGlyArgLeuIleAlaTyrLysAspLeuLeu

Ser

FIG. 1B-5

○ pHT3130
△ pHT3130ΔHpaII
▲ pHT3120
+ pHT3113a
× pHT3112a
● pHT3109
□ pHT3108
▽ pHT3107
■ pHT3104a

GRAM-POSITIVE BACTERIA REPLICON

CROSS-REFERENCES TO RELATED APPLICATIONS

This application is a 371 of PCT/FR92/00711, filed Jul. 20, 1992.

BACKGROUND OF THE INVENTION

1. Field of the Invention

The invention relates to a novel type of Gram-positive replicon and its use for the construction of recombinant vectors.

2. Discussion of the Background

The naturally occurring bacterial plasmids are usually endowed with a high degree of stability. If they are distributed randomly the theoretical probability (L) of producing a plasmid-free cell is given by the equation: $L=(\frac{1}{2})^{2n}$ (where n is the number of plasmid molecules per cell and it is supposed that 2n copies of the plasmid are present immediately prior to division). Thus, high copy number plasmids can be maintained in a stable manner following random distribution, whereas efficient mechanisms are necessary to prevent the loss of low copy number plasmids in the absence of selection pressure (Nordström and Austin, 1989 Annu. Rev. Genet. 23:37–69).

In Gram-negative bacteria, several systems involving maintenance functions for the plasmids have been described for low copy number plasmids such as F, P1 and R1. They comprise the hok/sok and ccd systems responsible for the post-segregational destruction of the cells which lose plasmids (Jaffé et al., 1985 J. Bacteriol. 163:841–849; Gerdes et al., 1986 Mol. Microbiol. 4:1807–1818) and true partition functions which ensure that each daughter cell receives a plasmid molecule (Austin and Nordström, 1990 Cell 60:351–354). Furthermore, auxiliary functions which allow random distribution of the replicons have been described. Examples include the site-specific recombination system of Col E1 (Summers and Sherrat, 1984 Cell 36:1097–1103) and the r locus of pSC101 (Tucker et al., 1984 Cell 38:191–201).

In Gram-positive bacteria, much less information is available concerning the functions required for the stable maintenance of the plasmids. In the plasmids with high or low copy numbers which replicate by a "rolling circle" mechanism through a single-stranded DNA intermediate (te Riele et al., 1986a EMBO J. 5: 631–637, 1986b Proc Natl. Acad Sci. USA 83:2541–2545; Gruss and Ehrlich, 1989 Microbiol. Rev. 53:231–241), the stability is coupled to replication and not to a discrete function. In the case of various known plasmids pUB110, pTA1060, pMV158 (Bron et al., 1991b Plasmid 19:231–241), and pLS11 (Chang et al., 1987 J. Bacteriol. 169 :3952–3962), the regions of stability are the "negative" origins controlling the conversion of the single-stranded DNA into double-stranded plasmid DNA The replication of these plasmids is guaranteed by a protein encoded in the plasmid. These plasmids are frequently unstable from a structural and segregational point of view when they are used as cloning vectors, and this is probably due to their particular mode of replication.

A second class of Gram-positive replicons comprises the large plasmids with low copy numbers, pTB19, pIP404 and pAMbeta1 (Imanaka et al., 1986 Mol. Gen. Genet. 205:90–96; Garneir and Cole, 1988 Plasmid 19:151–160; Swinfield et al., 1990 Gene 87:79–90). Their replication requires a protein encoded in the plasmid which does not share any homology with that of the plasmids whose replication involves a "rolling circle" mechanism. These plasmids do not accumulate single-stranded DNA during replication (Garnier and Cole, 1988 Plasmid 19:151–160; Janniére et al., 1990 Gene 87:53–61) and are structurally stable (Janniére et al., 1990 Gene 87:53–61).

No information is available concerning the potential partition functions of these plasmids with low copy numbers However, these functions are essential for their maintenance in sporulating Gram-positive bacteria such as the Bacillus species. During the differentiation stage of these bacteria, the spore compartment represents only about one sixth of the cell, and the probability of producing a plasmid-free spore is: $L=(\frac{5}{6})^{2n}$. A random distribution of the plasmids during sporulation may, consequently, lead to a serious loss of replicons (with n<10) in the spore population.

The sporulating Gram-positive bacterium *Bacillus thuringiensis* is known for its capacity to produce insecticidal toxins during sporulation (Lereclus et al., 1989b Regulation of Procaryotic Development. American Society for Microbiology, Washington D.C., 255–276). These parasporal proteins (delta-endotoxins) are each classified as being either CryI, II, III or IV as a function of their activity spectrum towards insect larvae (Höfte and Whiteley, 1989 Microbiol. Rev. 53:242–255). Different cry genes coding for delta-endotoxins active against various orders of insects have been cloned, and transformation by electroporation now makes possible the analysis of their expression in their natural host and the construction of strains obtained by genetic engineering exhibiting improved properties for insect control. *B. thuringiensis* exhibits a complex series of resident plasmids in most of the strains examined (Gonzalez et al., 1981 Plasmid 5:351–365; Lereclus et al., 1982 Mol. Gen. Genet. 186:391–398; Kronstad et al., 1983 J. Bacteriol 154:419–428). The quite widespread presence of these plasmids suggests very efficient stability and replication functions. Starting from that observation, cloning and characterization studies of small cryptic plasmids (Mahillon et al., 1988 Plasmid 19:169–173; Mahillon and Seurinck, 1988 Nucleic Adds Res. 16:11827–11828; McDowell et al., 1991 Plasmid 25:113–120) and the isolation of the replication regions of large plasmids (Baum et al., 1990 Appl. Environ. Microbiol. 56:3420–3428) and of two smaller plasmids pHT1000 and pHT1030 of 8.6 kb and 15 kb, respectively (Lereclus et al., FEMS Microbiol. Lett. 49:417–422) have been accomplished. pHT1030 was studied an account of its high segregation stability in *B. subtilis*, and a 2.9 kb DNA fragment including the stability and replication function of pHT1030 was used to construct the shuttle vector pHT3101 (Lereclus et al., 1989a FEMS Microbiol. Lett. 60:211–218; Debarbouilléet al., 1990 J. Bacteriol. 172:3966–3973).

SUMMARY OF THE INVENTION

With the objective of defining agents specific for the construction of cloning vectors and, optionally, expression vectors suited to the transformation of bacteria and, in particular, Gram-positive bacteria, the inventors have identified within the 2.9 kb DNA fragment of the plasmid pHT1030 (Lereclus et al., 1989a FEMS Microbiol. Lett. 60:211–218) a nuclectide sequence of about 2.6 kb and, within this sequence, different specific sequences for the stability and replication functions of plasmids used to transform Gram-positive bacteria The identification of these specific sequences has made it possible to define more precisely those which might be the elements of the 2.6 kb fragment which can be used in the context of the construction of recombinant vectors designed for the cloning and, optionally, the expression of sequences in Gram-positive bacteria for the purpose of modulating the behaviour of the vector in its host, for example for the purpose of modulating the stability and the number of copies of such vectors in a given bacterium. In fact, the inventors have observed that the stability function carried by the 2.6 kb fragment may be a nuisance in some applications such as the preparation of a recombinant vector used to transform bacteria themselves designed to be dispersed in the environment.

The results obtained by the inventors in the context of the invention thus make it possible to envisage the construction of vectors capable of being adapted to specific uses.

DESCRIPTION OF THE PREFERRED EMBODIMENTS

Different levels of adaptation may be envisaged in the light of the knowledge acquired by the inventors: As an example, the degree of replication of recombinant vectors constructed on the basis of the present invention in Gram-positive bacteria may be modulated.

Similarly, the segregational stability of these plasmids may be controlled by acting on certain specific parameters.

Another advantage of the invention results from the fact that the vectors used to transform Gram-negative bacteria, and particularly advantageously Gram-positive bacteria, use host proteins for their replication.

Hence, the object of the invention is a recombinant vector capable of replicating in Gram-positive bacteria, and optionally, of functioning as an expression vector in these bacteria The invention also relates to the different nucleotide fragments which can be used in the context of the construction of vectors suited for the transformation of Gram-positive bacteria involved in the stability and/or replication functions of the vector constructed. Host cells transformed by the vectors defined above as well as compositions involving the transformants are also included in the scope of the invention.

The invention also relates to a procedure for the preparation of the vectors as well as a procedure for the transformation of the cell strains.

A recombinant vector capable of replicating in Gram-positive bacteria is characterized in that it contains:

a) a nucleotide sequence I (SEQ ID NO:4) of *Bacillus thuringiensis* of about 2.6 kb included between the BalI-HpaI sites and corresponding to the sequence below defined by the nucleotides 1 to 2642 or,
  any fragment included in this sequence provided that it allows the replication of the recombinant vector when it is under the control of a promoter which is functional in Gram-positive bacteria or,
  any sequence which hydridizes with the complementary sequence of sequence I or the above fragment under conditions of high stringency, and b) at least one DNA sequence of interest inserted in phase with the above sequence.

A sequence hybridizing with the complementary sequence of sequence I or a fragment of I in the context of the invention hydridizes under conditions of high stringency defined by a medium containing 50% formamide, 660 mM of sodium chloride, 66 mM if sodium citrate, and an incubation for 12 hours at 42° C.

The *B. thuringiensis* strain from which the nucleotide sequence I (SEQ ID NO:4) is derived is the strain described in the publication of Lereclus et al. 1988 (FEMS Microbiol. Lett. 49:417–422).

The replication function, determined by the above sequence, may be modulated by the choice of the promoter. This promoter may be either the promoter present in the 2.6 kb fragment or any promoter capable of functioning in Gram-positive bacteria and preferably is a strong promoter of the veg type (Moran et al., Mol. Gen. Genet. 186:339–346).

A specific sequence for carrying out the invention, defined by its capacity to hybridize with the complementary sequence of sequence I, is capable of binding to this sequence or a fragment previously mentioned under the conditions of high stringency given above.

In the context of this invention a reverse sequence complementary to a given nucleotide sequence is said to be complementary to this nucleotide sequence The term "reverse" takes into account the restoration of the 5'-3' orientation of the nucleic acid which is also complementary to the given base sequence by the nature of the nucleotides it contains .

A sequence called "DNA sequence of interest" is a sequence capable of having economic value or an interest in the context of research, where it is desired to done or even to express it in a cell host which may be its natural host or even a different strain possessing an interest on account of its properties.

As an example, among the DNA sequences of interest, mention will be made of the DNA sequence coding for the delta-endotoxins of *B. thuringiensis* which are responsible for the production of crystals having a toxic activity towards insect larvae. In this connection, the DNA sequences called CryI, CryII, CryIII or CryIV described in the publication by Höfte and Whiteley (1989 Microbiol. Rev. 53:242–255) or any other Cry gene coding for a delta-endotoxin exhibiting an insecticidal activity are designated more particularly.

Other DNA sequences of interest are sequences which may be produced in Gram-positive bacteria on an industrial scale, for example, by fermentation or other procedures. As examples enzymes such as proteases, lipases and amylases, and protein hormones may be mentioned.

Other sequences of interest are constituted by heterologous sequences with respect to the cell host. For example, mention may be made of sequences coding for bacterial antigens which can be used as immunogens, for viral antigens, for example the HBs antigen or even for parasitic antigens such as those of *P. falciparum*.

According to a useful embodiment of the invention, the previously defined recombinant vector contains:

either a fragment II included in nucleotide sequence I and characterized in that it is defined by the BalI-AflII sites (nucleotides 1 to 1016) (SEQ ID NO:5) or the BalI-ScaI sites (nucleotides 1 to 1076) (SEQ ID NO:6), is about 1 kb long in *B. thuringiensis*, and is capable of ensuring the autonomous replication of the recombinant vector formed, or a sequence hybridizing with fragment II under conditions of high stringency and, at least one DNA sequence of interest inserted in phase with the above fragment.

The presence of this fragment designated by II (SEQ ID NO:5 or 6) ensures the autonomous replication of the recombinant vector formed and does so in Gram-positive bacteria whose host proteins are used for this replication.

According to another embodiment of the invention, the recombinant vector contains in phase with a functional promoter in the Gram-positive bacteria, a DNA fragment (also designated by the term replicon) included in the preceding sequence I (SEQ ID NO:4) and in the preceding sequence II, (SEQ ID NO:5 or 6) and corresponding to the nucleotide sequence III (SEQ ID NO:7) defined by SpeI-AflII sites comprising the nucleotides 312 to 1016 and a length of about 705 bp in B. thuringiensis, or a fragment hybridizing with the sequence complementary to sequence III under conditions of high stringency, or also a modified sequence III, provided that this fragment allows the vector formed to replicate in a Gram-positive bacterium when it is placed under the control of a promoter and, at least one DNA sequence of interest inserted in phase with the replicon.

In order to be functional as regards the replication of the vector, the nucleotide sequence III (SEQ ID NO:7) must be placed under the control of a promoter oriented in the same sense as sequence III (SEQ ID NO:7)

The sequences I, II and III (SEQ ID NO:4–7) contain a nucleic acid fragment of about 70 nucleotides, including a symmetric sequence (SEQ ID NO:8), the centre of symmetry of which is located at nucleotide 390. This sequence included between nucleotides 355 and 424 is imperfectly symmetrical and itself comprises a symmetrical sequence (SEQ ID NO:9) included between nucleotides 395 and 421 whose centre of symmetry is located at position 408.

The efficiency of replication of the recombinant vector according to the invention may be ensured by the use of a promoter in phase with sequence III (SEQ ID NO:7), making possible the autonomous replication of this vector and corresponding to or included in the nucleotide sequence IV (SEQ ID NO:10) defined by the BalI-NdeI sites, comprising the nucleotides 1 to 146 in B. thuringiensis, or a promoter constituted by a sequence hybridizing under conditions of high stringency with the sequence complementary to sequence IV, or also a modified sequence IV, provided that it defines a functional promoter under the above conditions, when it is in phase with the replicon.

Another recombinant vector according to the invention is characterized in that it contains, in addition to the sequence III (SEQ ID NO:7) or its derivatives as previously defined:

either a sequence containing elements necessary for the autonomous replication of the recombinant vector formed in a Gram-positive bacterium and elements contributing to the segregational stability of the vector, this sequence corresponding to or being included in the nucleotide sequence V (SEQ ID NO:11 or 12) defined by the BalI-SspI or BalI-SpeI sites comprising the nucleotides 1 to 304 and 1 to 314, respectively, of B. thuringiensis.

or a sequence hybridizing with the sequence complementary to sequence V under highly stringent conditions, or a sequence modified with respect to sequence V, provided that it conserves the functional properties of autonomous replication and stability of sequence V within the vector.

The invention also relates to a recombinant vector corresponding to one of the definitions described above, characterized in that it contains, in addition, a DNA fragment which ensures the stable maintenance of the recombinant vector in a Gram-positive bacterium, this fragment corresponding to either the nucleotide sequence VI (SEQ ID NO:13) defined by the HaeIII-HpaI sites comprising a length of about 1234 bp between nucleotides 1408 to 2642 of B. thuringiensis, or to any part of sequence VI which contributes to the stable maintenance of the vector in a bacterium, in particular a fragment comprising the HaeIII-AccI sequence of sequence VI of about 351 bp.

or to a DNA fragment modified with respect to the above fragments, provided that it conserves the capacity of sequence VI to confer stability on the vector formed, or to a fragment hybridizing with the sequence complementary to the above fragments.

The maintenance of the recombinant vector in a Gram-positive bacterium may be important depending on the uses for which this vector is designed.

For example, if Gram-positive bacteria with a vector of the invention comprising a sequence which it is desired to clone or express at a high level are transformed, it is important that the vector be stable. The desired stability may be a structural stability or a segregational stability, this latter being conferred or at least augmented by the presence of sequence VI or a fragment of this sequence under the conditions defined above.

Various vectors can be used to carry out the invention. Recourse will advantageously be had to a vector of the plasmid type and in particular to a vector implicating plasmid elements such as pUC18 or pUC19, in addition to the elements described above A recombinant vector according to the invention may additionally contain a specific selection system making it possible to select the Gram-positive bacteria containing the recombinant vector after transformation.

Such a system may be constituted by a gene coding for an enzyme necessary for the metabolism of the transformed bacterium In this connection, it may be genes responsible for the synthesis of metabolites such as tryptophan, uracil or thymine, or genes responsible for the use of sugars.

The selection system may also be constituted by a gene permitting a coloured selection of the recombinant clones, such as the lacZ or XylE genes or by a gene for resistance to a given antibiotic, for example a gene for resistance to erythromycin or ampicillin.

This last type of selection system is preferably selected when the transformants (bacteria transformed by the vector of the invention) are not intended for dispersal in the environment.

A preferred recombinant vector in the context of the invention is the plasmid pHT315 deposited on 7 Jun. 1991 with the CNCM (Collection Nationale de Cultures de Microorganismes in Paris, France) under number I-1111.

This plasmid which when it is integrated in a bacterium of the B. thuringiensis or B. subtilis type may produce a about 15 copies may also be used as starting plasmid and be modified for example by the incorporation of genes of interest which were discussed above.

Another useful vector in the context of the invention is the plasmid pHT3120 containing the BalI-AflII DNA sequence of about 1000 bp or the BalI-ScaI sequence of about 1076 bp of B. thuringiensis, recombined with the HaeIII-HpaI DNA sequence of about 1234 bp of B. thuringiensis.

In a preferred embodiment of the invention the recombinant plasmid comprises at least two DNA sequences of interest, each one being under the control of a cloning promoter and optionally an expression promoter, functional in Gram-positive bacteria.

The use of nucleotide sequences which have been described in the foregoing pages to clone and optionally express DNA sequences of interest requires that these nucleotide sequences are in the cis position with respect to the DNA sequences of interest.

The invention also refers to the different nucleotide sequences which have been described above under the references I, II, III, IV, V and VI (SEQ ID NO:4-7 and 10-12) and which are defined in the following terms:

- a nucleotide sequence I (SEQ ID NO: 4) of *B. thuringiensis* of about 2.6 kb included between the BalI-HpaI sites of the sequence below or,
- any fragment included in this sequence provided that it allows the replication of the recombinant vector when it is under the control of a functional promoter in Gram-positive bacteria or,
- any sequence hybridizing with the sequence complementary to the above sequence or fragment under highly stringent conditions;
- a DNA fragment included in sequence I and characterized in that it is a fragment defined by the BalI-AflII or BalI-ScaI sites (SEQ ID NO:5 or 6) of about 1016 bp (1.016 kb) of *B. thuringiensis*, capable of ensuring the autonomous replication of the recombinant vector formed, or any sequence hybridizing with the above fragment under conditions of high stringency;
- a DNA fragment or replicon included in sequence I and characterized in that it corresponds to or in that it is included in nucleotide sequence III (SEQ ID NO:7) defined by SpeI-AflII sites comprising the nucleotides 312 to 1016 in *Bacillus thuringiensis*, or a fragment hybridizing with the sequence complementary to sequence III or even a modified sequence III, provided that this fragment allows the replication of a recombinant vector in which it is integrated in a Gram-positive bacterium when it is in phase with a promoter;
- a promoter characterized in that it corresponds to or in that it comprises nucleotide sequence IV (SEQ ID NO:10) defined by the BalI-NdeI sites comprising the nucleotides 1 to 146 in *B. thuringiensis*, or corresponding to a sequence hybridizing with the sequence complementary to sequence IV or even of a modified sequence IV, provided that the promoter formed conserves its capacity to allow the autonomous replication of a recombinant vector when it is in phase with the replicon;
- a nucleotide sequence included in sequence I (SEQ ID NO:4) and itself comprising a promoter containing elements allowing the replication of a recombinant vector containing it in a Gram-positive bacterium and elements contributing to conferring on this vector its segregational stability, characterized in that it corresponds to or in that it is included in sequence V (SEQ ID NO:11 or 12) defined by the BalI-SspI or BalI-SpeI sites comprising the nucleotides 1 to 304 and 1 to 314 in *B. thuringiensis*, or a sequence which hybridizes under conditions of high stringency with the sequence complementary to sequence V, or even a modified sequence V, provided that it conserves the functional properties of autonomous replication and stability of sequence III;
- a DNA fragment capable of conferring on a recombinant vector its capacity to persist in a stable manner in a Gram-positive bacterium or to increase the stability of this vector when it is introduced in a Gram-positive bacterium, characterized in that it corresponds to nucleotide sequence VI (SEQ ID NO:13) defined by the HaeIII-HpaI sites comprising a length of about 1234 bp between the nucleotides 1408 to 2642 in *B. thuringiensis*, or comprising the HaeIII-AccI sequence of sequence VI of about 351 bp or a fragment modified with respect to the above fragments, provided that it conserves the properties of sequence VI involving the stability of a vector containing it in a Gram-positive bacterium, or even a fragment hybridizing with the sequence complementary to the above fragments.

The invention also relates to a Gram-positive bacterium, characterized in that it is transformed by a recombinant vector complying with the descriptions given in the preceding pages.

These transformed bacteria may be bacteria such as *Bacillus thuringiensis* or *Bacillus subtilis*, modified to clone an additional number of copies of DNA sequences coding for example for crystal proteins or delta-endotoxins.

Other bacilli which can be transformed are, for example, *B. cereus*, *B. sphaericus* or *B. megaterium*.

The agents of the invention are thus suited for the construction of recombinant Gram-positive bacteria appropriate for cloning and optionally for expressing a DNA of interest. Bacteria thus obtained may have uses in industry for producing large quantities of DNA or proteins, for example, in procedures involving fermentation steps to which bacteria such as *B. thuringiensis* lend themselves, or for the production of compositions for medical use.

The invention relates, in particular, to any recombinant bacterium capable of expressing bacterial antigens or immunogens, viral antigens such as the surface antigen of the hepatitis B virus (HBs), HIV antigens or immunogens, parasitic antigens such as those of *P. falciparum*.

The object of the invention is also a larvicidal composition active against insect larvae, characterized in that it contains as active ingredient bacteria transformed according to the previously described method in which the sequence of interest is a crystal gene coding for a delta-endotoxin active against the lepidoptera, coleoptera or diptera, in particular the cryI gene, cryII gene, the cryIII gene or the cryIV gene.

Generally, the recombinant vectors according to the invention can be used for the production of toxins, in particular polypeptides taxi towards insect larvae and in particular, towards the lepidoptera, coleoptera or diptera, this production of toxins being carried out through the intermediary of micro-organisms of the Gram-positive bacteria type.

The strains thus transformed constitute biopesticides.

Another use of the vectors and nucleotide sequences according to the invention is the cloning of selected DNA sequences. These cloned sequences may then be used in specific cell hosts to construct recombinant strains, for example recombinant *E. coli* strains.

The procedures for cell transformations, whether bacteria or other types of cells, with the recombinant vector according to the invention are the procedures usually used and such as described in the examples.

It will thus be possible to have recourse to a procedure such as electroporation described by Lereclus et al. (1989 FEMS Microbiol. Lett. 60:211–218).

Other characteristics and advantages of the invention will become apparent in the examples and in the Figures which follow.

BRIEF DESCRIPTION OF THE DRAWINGS

FIGS. 1A–1B Nucleotide sequence (SEQ ID NO:1) of the BalI restriction fragment of pHT1030 and deduced amino acid sequences of ORF1 (FIGS. 1A and 1B (SEQ ID NO:3)) and ORF2 (FIG. 1A (SEQ ID NO:2)).

The inverted repeat sequences capable of forming a stem and loop structure are underlined by arrows. The −35 and −10 regions of the putative promoter, found in the spaA locus are underlined. The ribosomal binding site and the potential start codon for the translation of spbB are shown in bold characters. The asterisks indicate the stop codon for translation.

Figure 2:
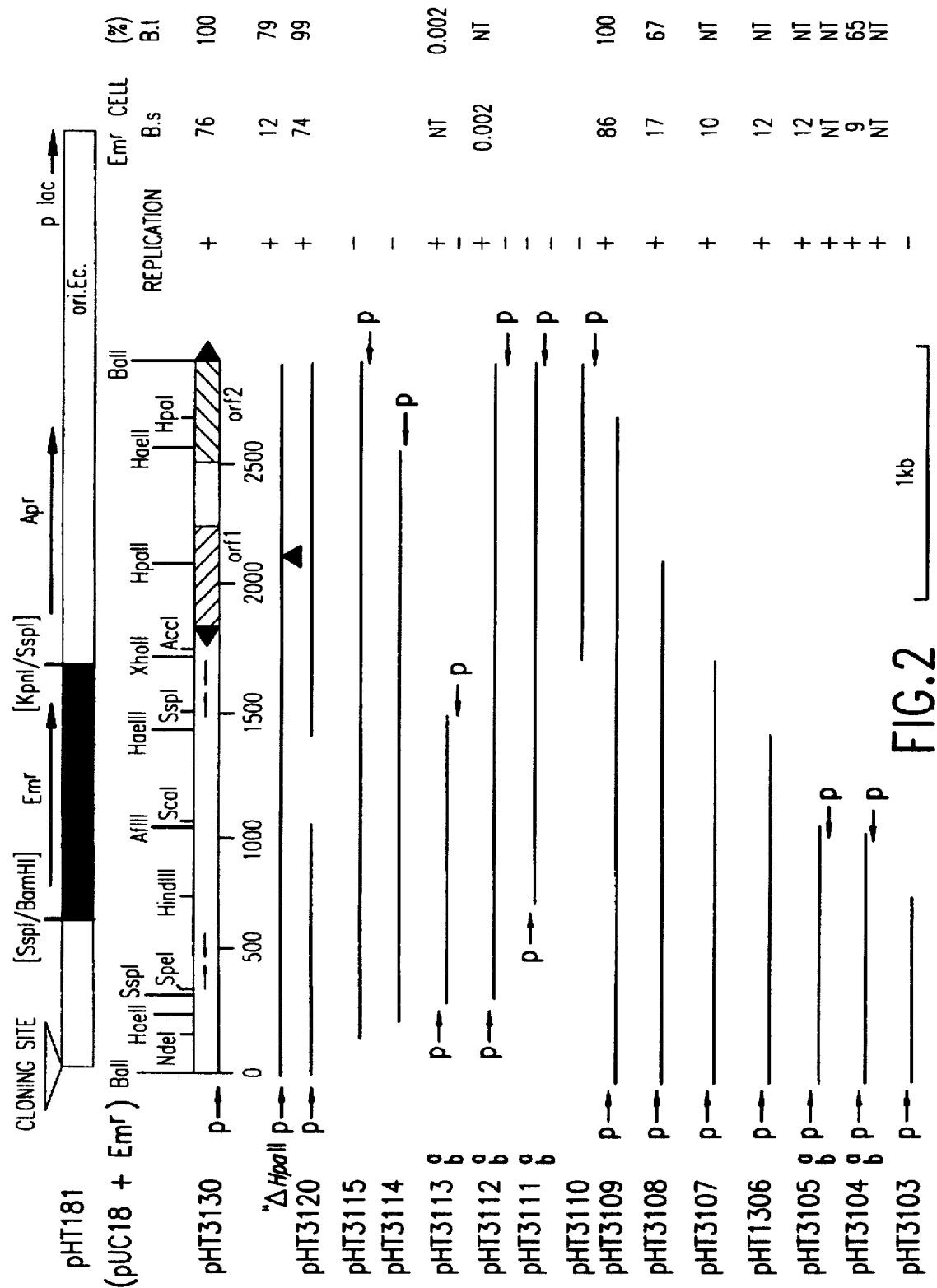

FIG. 2 Construction of deletion derivatives of pHT1030 and analysis of their replication and stability in the Bacilli.

The replication origin probe vector pHT181 described in the text is shown In the upper part of the Figure The restriction sites used to clone the 1.2 kb DNA fragment carrying the Em$^r$ gene in pUC18 are in parentheses. The location and orientation of the erythromycin (Em$^r$) and beta-lactamase (Ap$^r$) genes are shown by arrows.

The different restriction fragments of pHT1030 cloned into the cloning sites of pHT181 to give the plasmids pHT3103 to pHT3130 are shown under the map of pHT 81. These plasmids are constructed by elution of the appropriate restriction fragment from agarose gels and cloning in pHT181 cut by the appropriate enzymes. The recombinant plasmids carry the following restriction fragments: pHT3130, the entire 2.9 kb BalI fragment of pHT1030; pHT3130 HpaII the BalI fragment in which the HpaII site is removed (see text); pHT3120, the 1.1 kb BalI-ScaI fragment and the 1.5 kb HaeIII-BalI fragment cloned contiguously; pHT3115, the 2.7 kb NdeI-BalI fragment; pHT3114, the 2.3 kb HaeII fragment; pHT3113a and b, the 1.2 kb SspI fragment; pHT3112a and b, the 2.6 kb SpeI-BalI fragment; pHT3111a and b, the 2.2 kb HindIII-BalI fragment; pHT3110, the 1.1 kb AccI-BalI fragment; pHT3109, the 2.6 kb BalI-HapII fragment; pHT3108, the 2.1 kb BalI-HaII fragment; pHT3107, the 1.7 kb BalI-XhoII fragment; pHT3106, the 1.4 kb BalI-HaeIII fragment; pHT3105a and b, the 1.1 kb BalI-ScaI fragment; pHT3104a and h the 1 kb BalI-AflII fragment and pHT3103, the 0.7 kb BalI-HindIII fragment. All the constructions have been checked by restriction mapping of the recombinant plasmids. The location and orientation of the ORF1 (SEQ ID NO:1) and ORF2 are shown by a compartment and an arrow, as shown by the nucleotide sequence shown in FIG. 1. The convergent arrows symbolize the groups of inverted repeat sequences. p and the arrow indicate the position and the orientation of the lacZ promoter of pUC18.

Construction of the plasmid pHT3120

The plasmid pHT3130 (FIG. 2) is digested, on the one hand, with the enzymes KpnI and ScaI and, on the other, with the enzymes HaeIII and BamHI. The 1.1 kb KpnI-ScaI restriction fragment (containing the BalI-ScaI segment of the replication region) and the 1.5 kb HaeIII-BamHI restriction fragment (containing the HaeIII-BalI segment of the stability region) are obtained and purified separately on agarose gel. The two restriction fragments are ligated together in the presence of the vector pHT181 digested by the enzymes KpnI and BamHI and in the presence of DNA ligase.

The ligation mixture is used to transform the E. coli strain TG1 and the recombinant clones are selected on LB medium containing ampicillin (100 µg/ml) and X-gal. Among the transformants, a white Ap$^r$ colony was isolated and the analysis of its plasmid DNA indicates that the clone carries a plasmid with the expected restriction map. This plasmid called pHT3120 does not contain the 0.3 kb ScaI-HaeIII fragment of pHT3130.

The replication of each of the deletion derivatives of pHT1030 was tested by transformation of B. subtilis and B. thuringiensis + indicates transformant clones resistant to erythromycin were obtained; −indicates that Em$^r$ transformants were not obtained. The segregational stability of each of the recombinant plasmids was tested in B. subtilis (B.s) and B. thuringiensis (B.t) in an LB medium as described in Experimental Procedures. The percentages of clones which were Em$^r$ after about 25 generations (in the case of B. subtilis) and 40 generations (in the case of B. thuringiensis) without selection pressure have been, indicated. NT: not tested.

Figure 3:
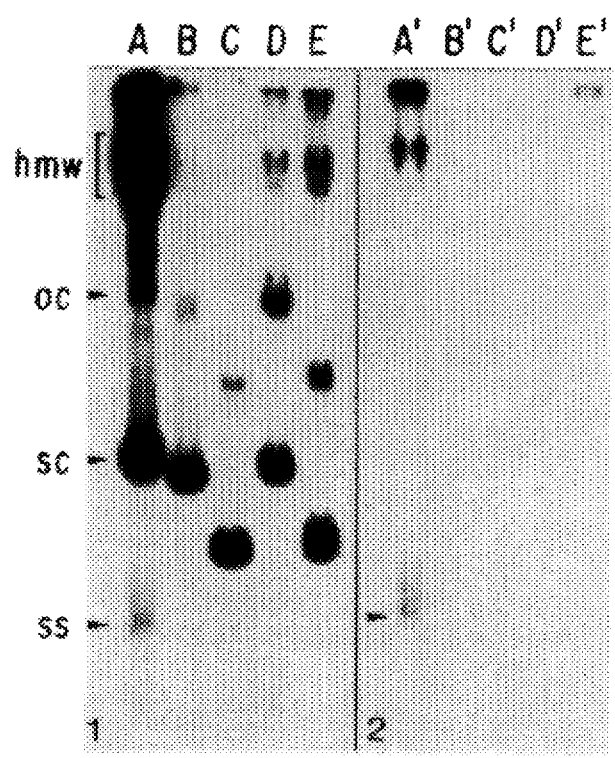

FIG. 3 Analysis of the production of single-stranded DNA in cells containing deletion derivative of pHT1030.

Cells lysates of B. subtilis containing pHV33 (lanes A and A'), pHT3130 (lanes B and B') or pHT3104a (lanes C and C') and of B. thuringiensis containing pHT3130 (lanes D and D') or pHT3104a (lanes E and E') were separated by agarose gel electrophoresis.

Gel 1 was transferred to a nitrocellulose filter after denaturation and gel 2 without denaturation. The filters were then hybridized with pUC18 labelled with 32p which contains DNA sequences also present in all of the plasmids analysed. The Figure shows the autoradiographs obtained after exposure. ss, sc, oc and hmw indicate the single-stranded, superhelical, open circle (or dimeric) forms and high molecular weight of the pHV33 DNA, respectively.

Figure 4:
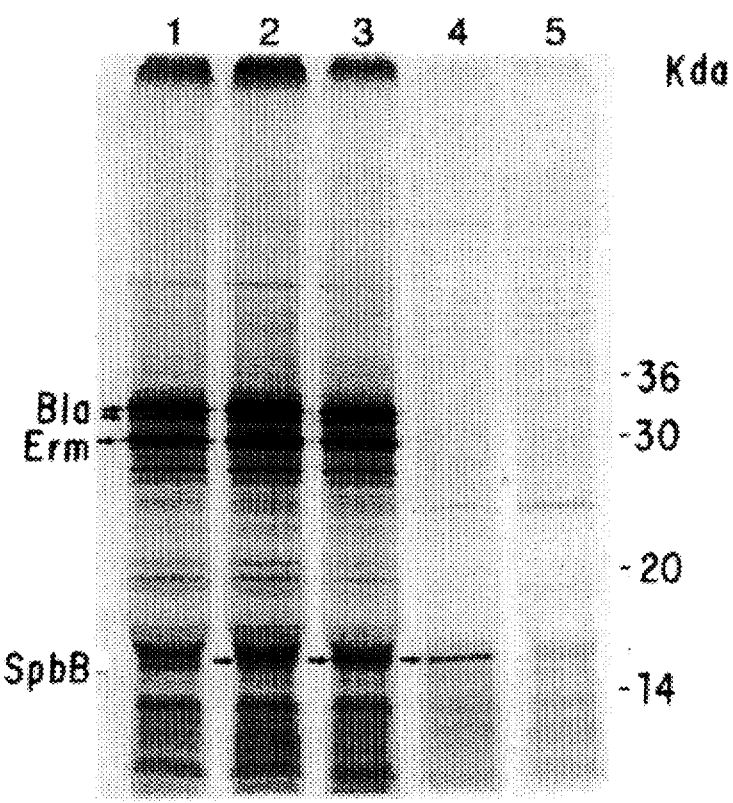

FIG. 4 Expression of the spbB gene in an in vitro E. coli transcription-translation system.

The autoradiographs of the labelled polypeptides labelled with [$^{35}$S]-methionine, separated on a 12.5% acrylamide gel produced by: lane 1, pHT181; lane 2, pHT3109; lane 3, pHI3114; lane 4, a 464 bp BstUI fragment isolated from pHT3130 and containing the spbB gene: lane 5, the 462 bp BstUI fragment isolated from pHT3130ΔpaII and containing an interrupted spbB gene. Erm, Bla and SpbB indicate the gene products of erm bla and spbB, respectively. The size of the molecular weight markers of the peptides is indicated (kDa).

Figure 5A:
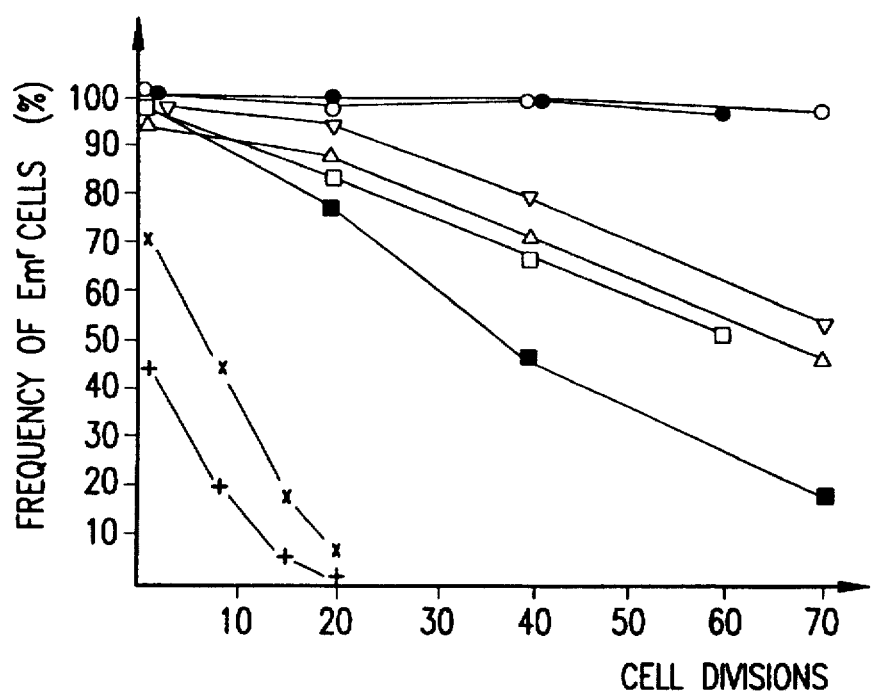
Figure 5B:
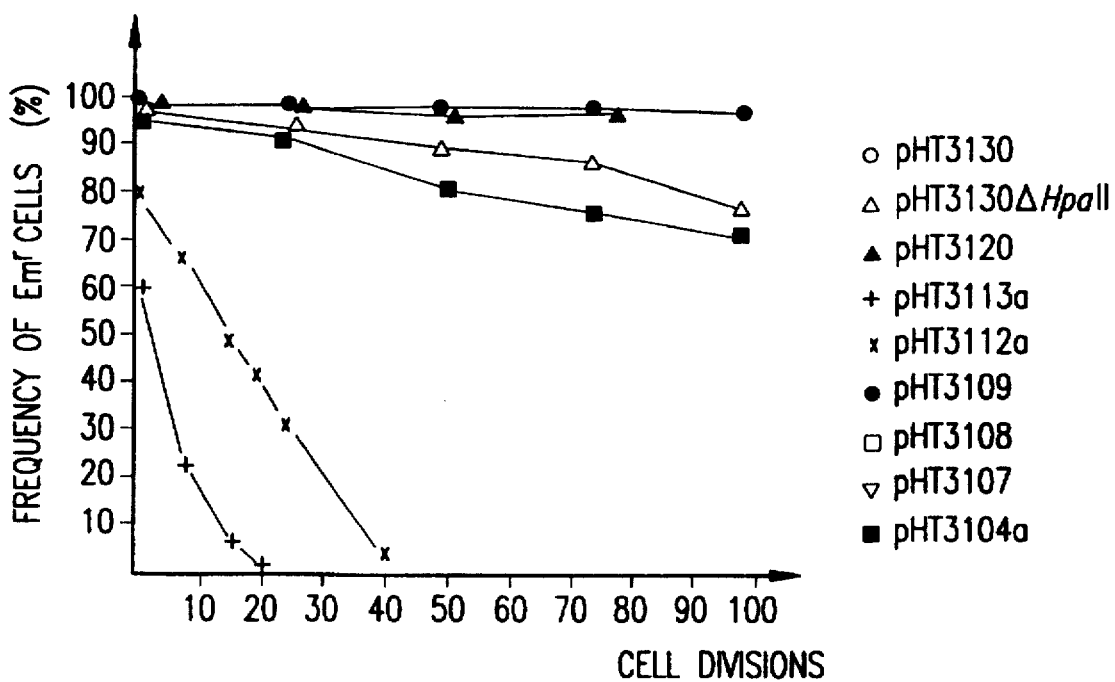

FIGS. 5A–5B Segregation stability of the deletion derivatives of pHT1030 during vegetative growth.

Exponentially growing cells of B. subtilis (table A) and B. thuringiensis (table B) carrying various plasmids were evaluated with respect to their segregational stability in a non-selective BHI medium as described in Experimental Procedures. No significant differences were observed in the growth levels between cells harboring the various plasmids. The symbol for each plasmid is indicated in Table B.

Figure 6A:
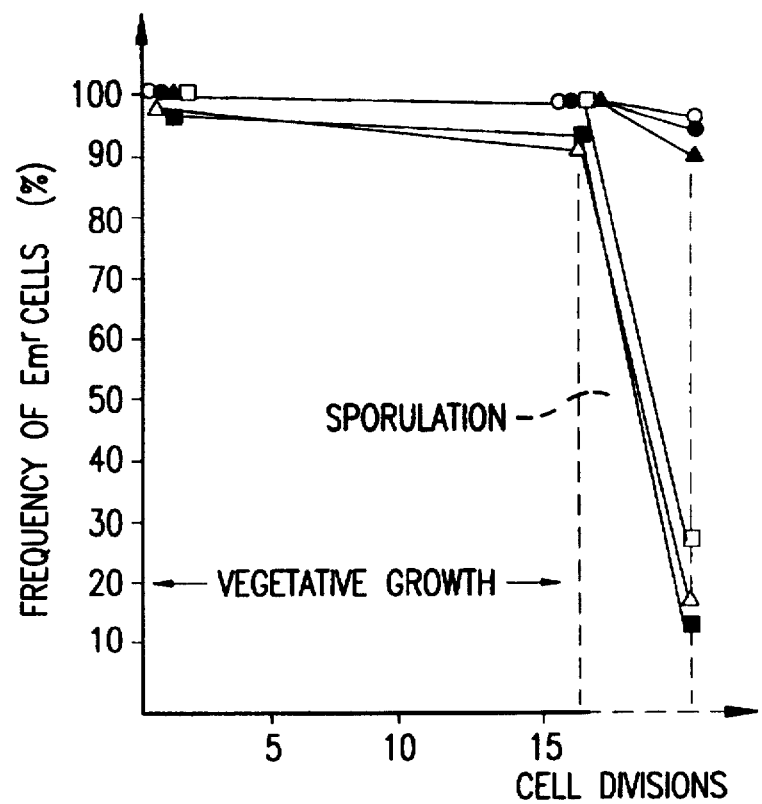
Figure 6B:
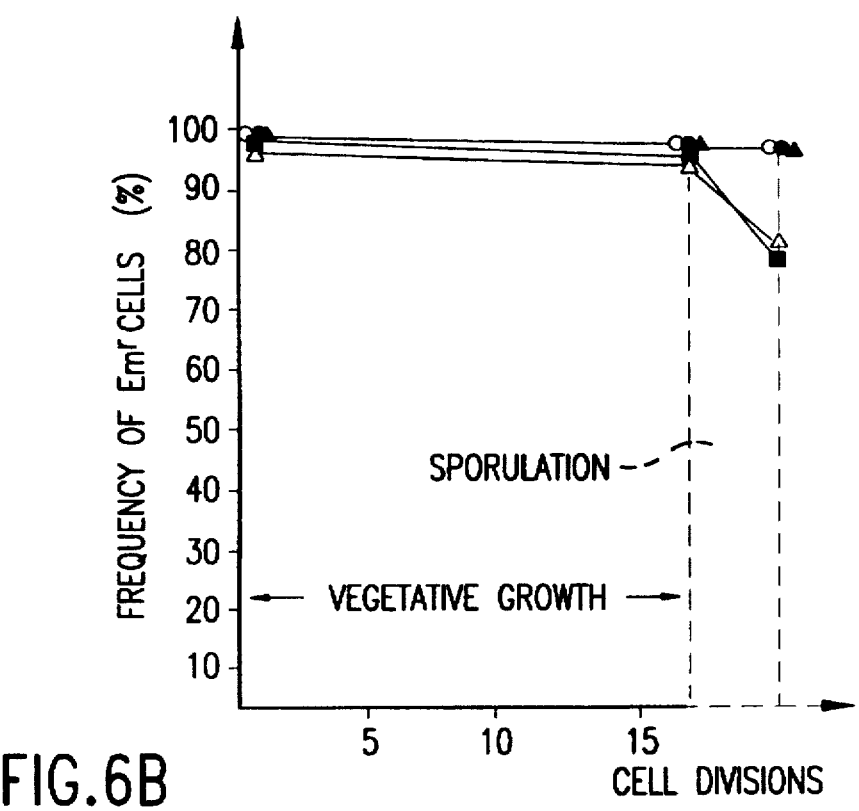

FIGS. 6A–6B Segregation stability of the deletion derivatives of pHT1030 during sporulation.

The stability of the plasmid was evaluated in sporulating B. subtilis (table A) and B. thuringiensis (table B) cells carrying various plasmids in a non-selective HCT or SP medium as described in Experimental Procedures. The symbol used for each plasmid is indicated in FIG. 5.

Figure 7:
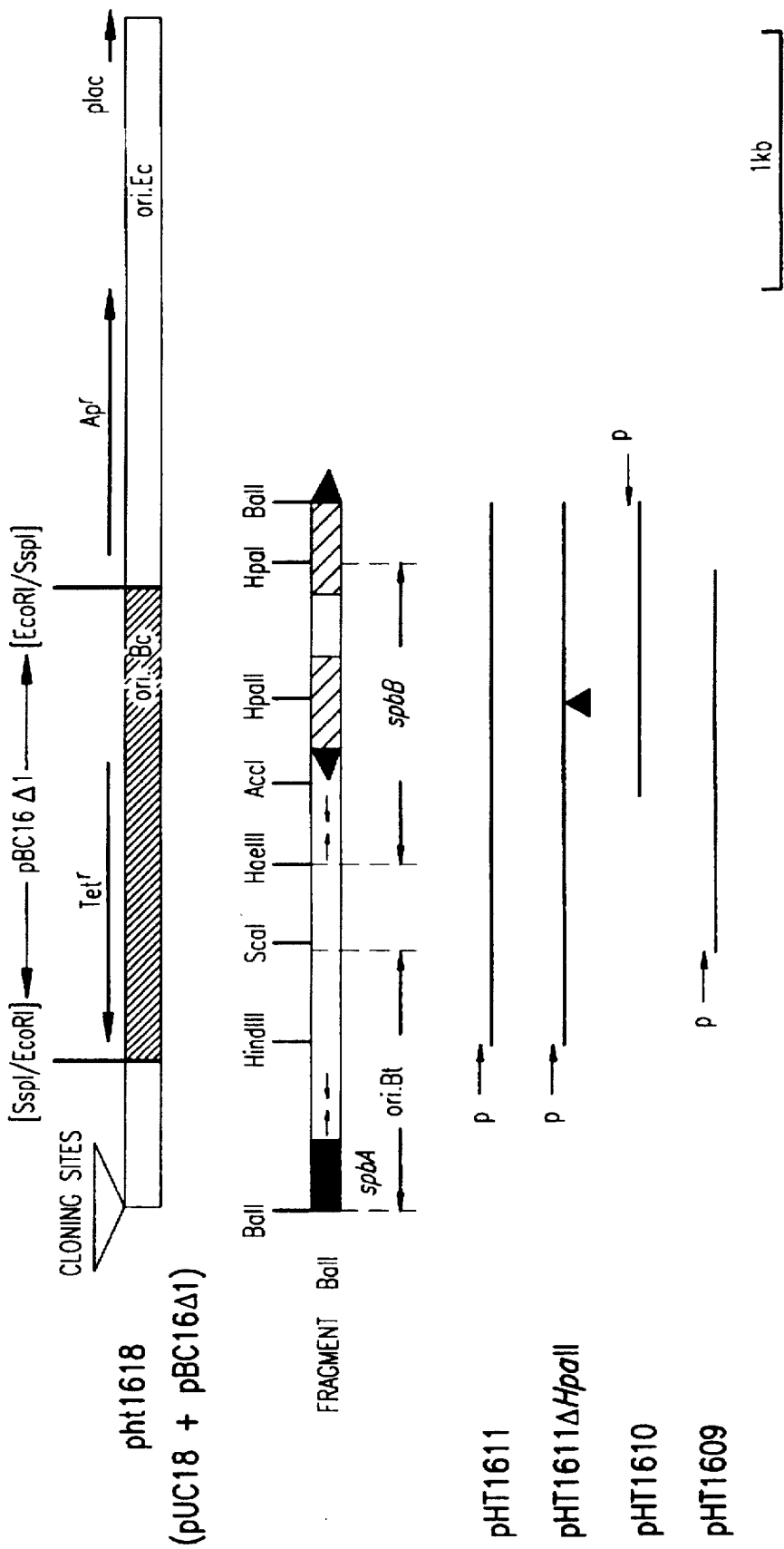

FIG. 7 Construction of the pBC16 variants carrying regions of the spbB locus.

The physical map of the recombinant plasmid pHT1618 is shown in the upper part of the Figure The replication regions of pBC16 and pUC18 are labelled ori.Bc and ori.Ec, respectively. The positions and orientations of the genes conferring resistance to tetracycline (Tet$^r$) and ampicillin (Ap$^r$) are shown by arrows. The restriction sites used for the cloning of pBC16 1 (2.9 kb EcoRI segment whose ends have been filled by the Klenow fragment of the DNA polymerase I) in pUC18 are in parentheses The physical and genetic organization of the BalI DNA fragment is shown in conformity with the results described in the text. spbA and spbB show the positions of the loci. ori.Bt represents the minimal replicon of pHT1030. The other symbols are as described in the legend to FIG. 2.

The full lines represent the segments of the BalI fragment cloned into the cloning sites of pHT1618 to give the plasmids pHT1609 to pHT1611. The DNA segments were purified separately on agarose gel and cloned in pHT1618 cut by appropriate enzymes. pHT1611 bears the 2.2 kb HindIII—HindIII fragment isolated from pHT3130 and corresponding to the 2.2 kb HindIII—HindIII fragment of pHT1030 (the second HindIII is derived from th pHT3130 polylinker). pHT1611 paII bears the 2.2 kb HindIII—HindIII fragment isolated from pHT3130 HpaII. pHT1610 bears the 1.1 kb AccI-BalI fragment and pHT1609 bears the 1.6 kb ScaI-HpaI fragment of pHT1030. The constructions were checked by restriction mapping of the recombinant plasmids. p and the arrow indicate the position and the orientation of the lacZ promoter of pUC18.

Figure 8:
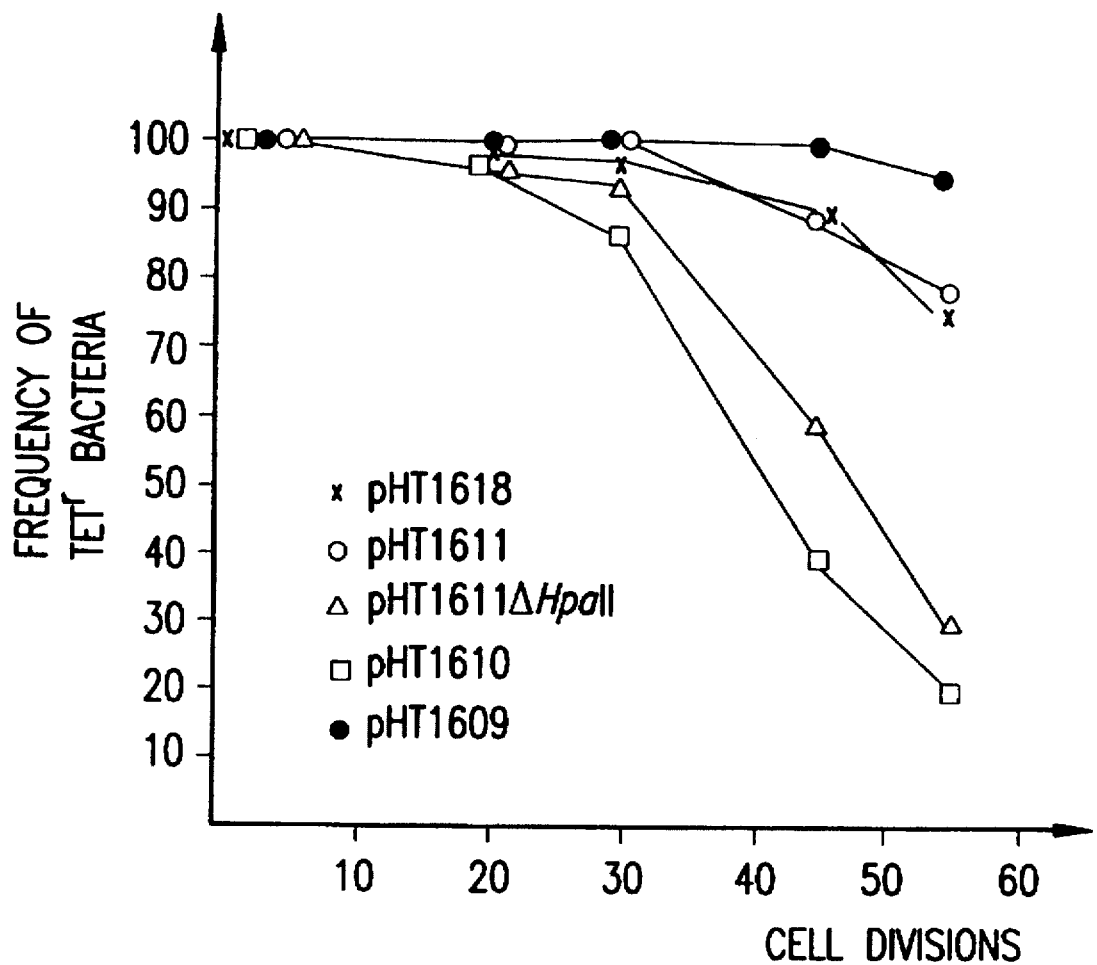

FIG. 8 Stability of the pBC16 variants bearing the spbB regions.

Exponentially growing cells of *B. subtilis* harboring various plasmids were evaluated with respect to segregational stability in a non-selective BHI medium as described in Experimental Procedures. The symbol of each plasmid is indicated in the Figure.

Figure 9:
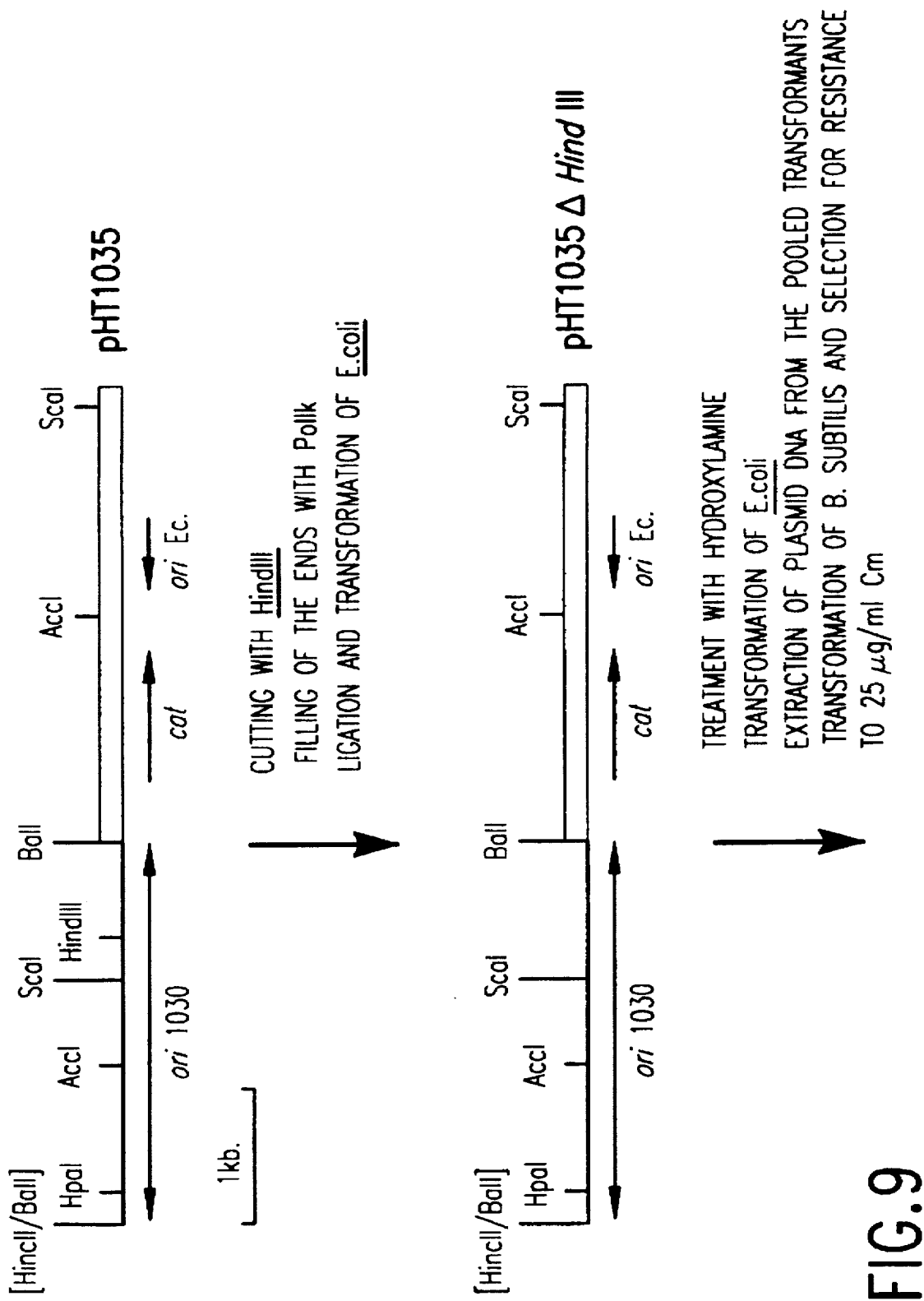

FIG. 9 Elimination of the HindIII site of pHT1035 and selection of variants with a high copy number.

The HindIII site of pHT1035 was removed as shown in the first part of the Figure. In vitro mutagenesis of pH1035ΔHindIII was carried out by treatment with hydroxylamine as described previously (Humphreys et al., 1976 Mol. Gen. Genet 145:101–108). 20 μg of the treated DNA were used to transform the *E. coli* strain JM83. Approximately ten thousands Cm-resistant clones (5 μg/ml) were collected and the plasmid DNA was extracted. Subsequently, competent *B. subtilis* cells were transformed by about 10 μg of plasmid DNA and spread an LB gelose containing 25 μg of Cm per ml. From about one hundred $Cm^r$ clones obtained, fourteen were tested for their plasmid content. Agarose gel electrophoresis of the DNA preparations indicated that nine of them harbored plasmids with a number of copies higher than the parent plasmid pHT1035 HindIII. Two clones harboring plasmids with high and intermediate numbers of copies were selected. The arrows above "cat" and "ori.Ec" indicate the direction of transcription of the cat gene and the direction of replication of pBR322, respectively. The double arrow above "ori1030" indicates that the orientation of replication of pHT1030 is not known. The unique restriction sites of the plasmids are shown in bold characters.

Figure 10:
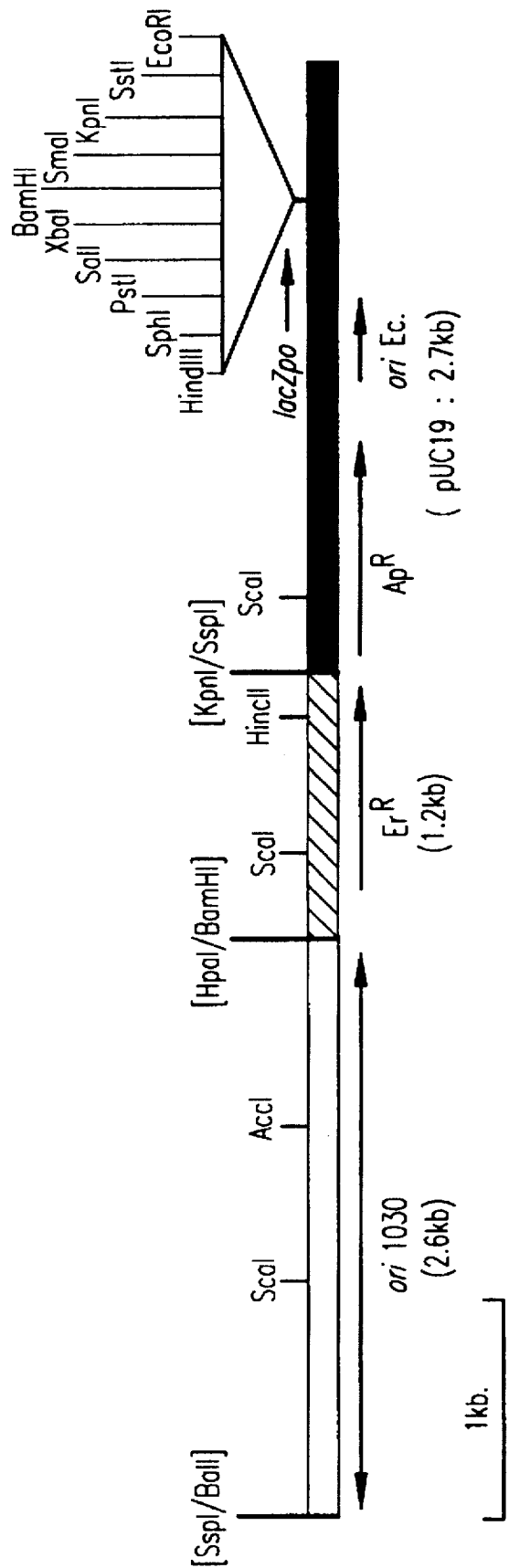

FIG. 10 Construction of the shuttle vectors pHT304, pHT315 and pHT370.

The 2.6 kb HpaI-BalI DNA fragment carrying the replication and stability regions of pHT1030 was isolated and purified separately from pHT1035 HindIII, pHT1035-15 HindIII and pHT1035-70 HindIII. A 1.2 kb KpnI-BamHI carrying the constitutive erm gene derived from Tn1545 (Trieu-Cuot et al., 1990 Nucleic Acids Res. 18:3660) was isolated in the form of a Asp718-BamHI and the ends were made blunt with PolIk. Each HpaI-BalI fragment was cloned at the SspI site of pUC19 with the fragment containing the erm gene by triple ligation. The three ligation mixtures were used separately to transform the *E. coli* strain JM83, and the recombinant clones were selected on LB gelose plates containing Ap (100 μg/ml) and Er (150 μg/ml). The shuttle vectors pHT304, pHT315 and pHT370 in which the different DNA fragments are cloned at the same place in the same orientation were selected by restriction mapping. The sites destroyed at the blunt junctions are shown in parentheses. The arrows above "$Er^R$" and "$Ap^R$" and before "lacZpo" indicate the direction of transcription of the erm, bla and lacZ genes, respectively. The number of copies of the plasmid in *B. thuringiensis* is indicated for each vector. The other symbols are as described in the legend t o FIG. 9.

Figure 11:
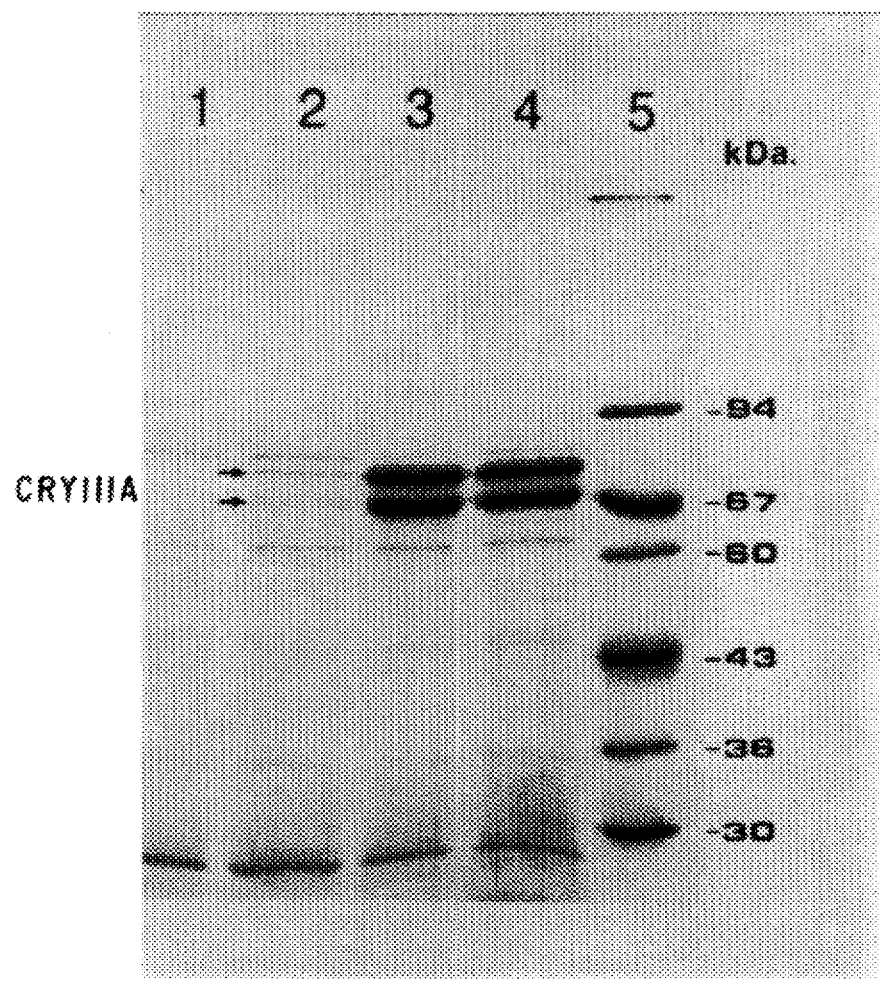

FIG. 11 Analysis of the proteins of the *B. thuringiensis* transformants expressing the cryIIIA gene.

Spore-crystal preparations were obtained and analysed by SDS-PAGE and stained with Coomassie Blue as was described previously (Lereclus et al., 1989a FEMS Microbiol. Let. 60:211–218). An aliquot sample (20 μl) was loaded into each well. Lanes 1, 2, 3, 4: kurstaki HD1 CryB strain containing pHT315; pHT304 cryIIIA; pHT315 cryIIIA and pHT370 cryIIIA, respectively. Lane 5: molecular weight markers. The arrows indicate the crystal components of 73 and 67 kDa.

EXAMPLES

1ST Example

Analysis of the Nucleotide Sequence of the Replicon pHT1030.

The 2.9 kb BalI DNA fragment containing the replication region of pHT1030 (Lereclus et al., 1988 FEMS Microbiol. Lett. 49: 417–422) was inserted in both orientations at the SmaI site of the pUC18 vector and different DNA fragments were subcloned into the phages M13mpl8 and M13mpl9 for sequencing. Overlapping deletions were also obtained from the entire BalI fragment cloned in M13mpl9 using the procedure of Dale et al.(1985, Plasmid 13:31–40). The synthesis of specific oliganucleotide primers, deduced from the results of preliminary sequencing has made it possible to obtain more information concerning the sequences starting from suitable recombinant phages used as matrices. The complete nucleotide sequence (FIG. 1) (SEQ ID NO:1) of the 2872 bp BalI fragment was determined on both DNA strands. The total dA+dT content of the DNA fragment of 63% is very similar to that of the *B. thuringiensis* chromosome: 63.6% (Kaneko et al., 1978 Microbiol. Immunol. 22:639–641).

The sequence comprises two major complementary inverted repeat sequences which were able to form potentially stable hairpin loop RNA structures. The largest of the two regions comprises 70 nucleotides with a centre of symmetry situated at nucleotide 390. The free energy of interaction calculated according to Tinoco et al. (1973, Nature (London) New Biol. 246:40–41) is −156.5 kj/mole The two symmetric sequences are repeated imperfectly and the mapping of the DNA region in FIG. 1A between the positions 392 and 425 itself contains a pair of inverted repeat sequences having a calculated free energy of interaction of −66.1 kJ/mole. The second major group of complementary sequences is situated between the positions 1572 and 1598. Eleven nucleotides are repeated perfectly and can form a hairpin loop structure with a calculated free energy of interaction of −95.4 kj/mole.

The nucleotide sequence shown in FIG. 1A (SEQ ID NO:1) was examined in both directions for the regions coding for a potential protein. The latter were defined on the basis of dimensions (>70 codons) and suitable translation initiation signals (McLaughlin et al., 1981 J. Biol. Chem. 256:11283–11291). Only two supposed open reading frames (ORF open reading frames) were found, they code in opposite directions (FIG. 1). The presumed start codons of ORF1 (UUG) and ORF2 (AUG) are preceded by appropriate ribosomal binding sites corresponding to the 3'-OH of the 16S r RNA of *B. subtilis* (McLaughlin et al., 1981). The free energies of interaction, deduced according to Tinoco et al.(1973) are −57.5 kJ/mole (ORF1) and −51 kJ/mde (ORF2). ORF1 codes for 134 amino acids starting at position 2193 and terminating at position 1792 (SEQ ID NO:3). The calculated molecular mass of the supposed ORF1 product is 15524. ORF2 codes for a polypeptide (SEQ ID NO:2) starting at position 2521, interrupted at position 2872 by cloning of the BalI DNA fragment.

Comparison of the deduced ORF1 and ORF2 sequences (SEQ ID NO:3 and 2) with the sequences of proteins available in the Gene Libraries/EMBL and NBRF, and specifically those encoded in plasmids, did not reveal any significant homology.

Potential promoters for ORF1 and ORF2 have been identified by comparison of the regions upstream from ORF1 and ORF2 with known consensus regions of *B. subtilis* promoters (Moran, 1986 Regulation of Procaryotic Development. American Society for Microbiology, Washington D.C., 167–184) (FIG. 1). The region of symmetry situated between positions 1572 and 1598 may correspond to a transcription terminator for ORF1. When it is read on the same strand as ORF1, the potential hairpin loop RNA structure is followed by a segment of 6 U residues interrupted by two A residues. This structure is reminiscent of a rho-independent terminator.

Determination of the Minimal Replication Region of pHT1030.

To test the replication activity of DNA fragments derived from the BalI fragment of pHT1030, the replication origin probe vector pHT181 was constructed, in which a 1.2 kb DNA fragment carrying a gene conferring resistance to erythromycin on Gram-positive bacteria (Trieu-Cuot et al., 1990 Nucleic Acids Res. 18 :3660) was cloned at the SI site of pUC18 (FIG. 2). Like pUC18, pHT181 can be used for cloning experiments in *E. coli*, given that the Em$^r$ gene inserted at the SspI site interrupts neither the cloning sites of the polylinker nor the beta-lactamase gene. Thus, the entire BalI DNA fragment and several fragments of the latter were cloned in pHT181, and their replication was tested in *B. subtilis* and *B. thuringiensis* (FIG. 2). The smallest DNA segment capable of supporting the replication of recombinant plasmids in the Bacilli was a 705 bp SpeI-AflII (nt 312–1016, FIG. 1 (SEQ ID NO:7). However, the replication capacity of this DNA segment was dependent on its orientation with respect to the lacZ promoter of pUC18. pHT3112a and pHT3113a were capable of transforming Bacilli for resistance to erythromycin, but transformants were not obtained with pHT3112b, pHT3133b, pHT3114 and pHT3115 in which the fragment is in the opposite orientation.

This result suggests that, in the case of pHT3112a and pHT3113a, the lacz promoter region situated upstream from the cloning sites provides a promoter activity which had been lost in these deletion derivatives. The essential promoter for the autonomous replication of pHT1030 might then be present in the 146 bp BalI-NdeI DNA fragment (nt 1–146), FIG. 1 (SEQ ID NO:10). Possible −35 (TTGATT) and −10 (TAAAAT) regions are found in this DNA segment at nucleotide positions 75–80 and 98–103, respectively (FIG. 1) (SEQ ID NO:1). This is in agreement with the fact that the BalI-AflII and BalI-ScaI fragments of 1 kb (SEQ ID NO:6) provide efficient replication in the Bacilli when they are cloned in one or other orientation in pHT181 to give the plasmids pHT3104a, b and pHT3105a, b (FIG. 2). Thus, the minimal region ofpHT1030 conferring autonomous replication is completely included in the 1016 bp BalI-AflII restriction fragment (SEQ ID NO:5) cloned in the plasmids pHT3104a, b (FIG. 2). The two major characteristics of this replication region are the presence of the sequence 70 nucleotides long and symmetrical about a point, and the apparent absence of any protein encoded by a plasmid and required for replication. The longest ORF (95 codons) found in this DNA region does not exhibit an appropriate translation initiation signal.

Replication Behaviour of the Deletion Derivatives of pHT1030.

The integrity of the replication functions of the minimal replicon cloned in pHT3104a was verified by comparison of its replication characteristics with those of pHT3130, which is the entire BalI DNA fragment cloned in the replication origin probe vector pHT181 (FIG. 2).

The number of copies of the two plasmids was determined. In both *B. subtilis* and *B. thuringiensis* pHT3130 and pHT3104a showed an identical number of copies estimated at 4.2 +/−0.6 covalently closed circular plasmid molecules per chromosome equivalent. It may be concluded that the required functions for the control of the number of copies are all present in the minimal replicon cloned in pHT3104a.

Another approach to test the integrity of the replication functions of pHT3104a consisted in determining its production of single-stranded DNA Many plasmids derived from Gram-positive bacteria replicate by a mechanism of the "rolling circle" type and the deletion of the negative origin sequence leads to the accumulation of single-stranded plasmid DNA (Gruss and Ehrlich, 1989 Microbiol. Rev. 53:231–241; Devine et al., 1989). pHT3100 and pHT3104a were tested for the production of single-stranded plasmid DNA by using the procedure described by te Riele et al. (1986a Proc Natl. Acad. Sci. USA 83:2541–2545). Total DNA preparations were loaded on to agarose gels, separated and transferred on to nitrocellulose filters with or without prior denaturation with NaOH.

The results of their hybridization with a pUC18 plasmid labelled with 32p are presented in FIG. 3. pHT3130 and pHT3104a did not produce detectable quantities of single-stranded DNA in either *B. subtilis* or *B. thuringiensis*. Furthermore, Gruss and Ehrlich (1988) showed that the insertion of foreign DNA into plasmids of the "rolling circle" type leads to the formation of multimers in tandem of high molecular weight (HMW. By comparison with the hybrid plasmid pHV33 of the "rolling circle" type, significant quantities of HMW were not found with pHT3100 and pHT3104a in *B. subtilis* (FIG. lanes B and Q and only low levels when these plasmids were in *B. thuringiensis* (FIG. 3, lanes D and E). These results strongly suggest that pHT1030 and its deletion derivatives do not replicate by a single-stranded DNA intermediate and show that the replication behaviour s of pHT3130 and pHT3104 are not significantly different in *B subtilis* and *B. thuringiensis*. Thus, it may be concluded that the essential replication functions of pHT1030 are conserved in the minimal replicon cloned in pHT 3104a.

Segregational Stability of the Deletion Derivatives of pHT1030.

To determine the DNA region necessary for the segregational stability of pH1030, the maintenance of a selection of the deletion derivatives Rep$^+$of this replicon was characterized in *B. subtilis* or *B. thuringiensis* in an LB medium without antibiotic selection (FIG. 2).

The most striking instability results from the deletion of small BalI-SspI or BalI-SpeI DNA fragments (SEQ ID NO:11 or 12). pHT3112a and pHT3113a from which these fragments are missing were rapidly lost in the absence of selection pressure. Consequently, this short DNA fragment, which has been shown above to be linked to the replication function of pHT1030, is also implicated in the stability of the replicon. This region of 300 bp has been designated spbA (stability of the plasmid in the Bacilli).

The other Rep$^+$plasmids were more stable in *B. thuringiensis* than in *B. subtilis*. This effect of the host will be discussed hereafter.

Independently of the host bacterium, a partial deletion of ORF2 (pHT3109) and a deletion of the ScaI-HaeIII fragment (pHT3120) gave plasmids as stable as pHT3130. However, the plasmids in which ORF1 is partially or totally deleted (pHT3108 to pHT3104) show a significantly reduced stability. These results suggest that the 1234 bp HaeIII-HpaI DNA fragment (SEQ ID NO:13) containing ORF1 is involved in the maintenance of pHT1030 in the two species of Bacilli. This locus is designated spbB. To determine whether a potential spbB gene product is responsible or not for the stability of pHT1030, a plasmid bearing an interrupted spbB gene was constructed. The unique HpaII site of the 2.6 kb BalI fragment of pHT1030 was removed by cutting with HpaII and filling of the ends using the Klenow fragment of DNA polymerase I, and the modified BalI fragment was cloned in pHT181 to give the plasmid pHT3130 HpaII. The modification of the restriction site was confirmed by nucleotide sequencing by using a suitable synthetic oligonucleotide primer. Whereas mutagenesis ought to lead to the addition of 2 bp, nucleotide sequencing revealed that, for unknown reasons, 2 bp were lost from pHT3130Δ. HpaII (SEQ ID NO:14) (the DNA sequence 5'-TAAATGGGA-3' has replaced a sequence which is the same as 5'-TAAATGGGA-3', but which has an additional CC between TAAT and GGGA at the nucleotide positions 2070–2080). Nonetheless, this modification causes a shift in the reading frame in the presumed spbB gene (ORF1) moving a nonsense codon 14 codons upstream in the reading frame. pHT3130 HpaII had a lower segregational stability than pHT1030 and one similar to that of the deletion derivatives pHT3108 to pHT3104 (FIG. 4).

These experimental data might point to the implication of a polypeptide encoded in spbB in the maintenance of pHT1030 in the Bacilli. The expression of the spbB was tested in an in vitro E. coli transcription-translation system (FIG. 4). A 564 bp BstUI DNA fragment (located between the nucleotide positions 1692 and 2256 of FIG. 1) containing the supposed spbB gene was purified separately from each of pHT3130 and pHT3130ΔHpaII and was tested in parallel. Only the BstUI DNA fragment from pHT3130 directed the expression of an additional protein of 15 kDa (FIG. 4, lane 4). Furthermore, the in vitro transcription-translation of the entire plasmids pHT3109 and pHT114 led to the appearance of a protein exhibiting the same apparent size. This protein was absent from the assay containing pHT181. The apparent size of the SpbB polypeptide is in agreement with the molecular weight calculated from the nucleotide sequence of ORF1. These results demonstrate that the integrity of this DNA sequence is required for the stability, and probably for the expression, of the encoded protein.

Since the absence of spbB does not affect the apparent replication behaviour of the plasmids, the spbB gene product is only implicated in stability.

Does the Locus have an Active Stabilizing Function? Nordström and Austin (1989, Annu. Rev. Genet. 23:37–69) defined two classes of stability factors: those which ensure a random distribution of the plasmid during cell division and those which lead to a better than random stability.

In order to determine to which class the spbB locus belongs, it was consequently necessary to establish the frequency of loss of plasmids per generation in the absence and presence of spbB Comparison of these frequencies with the theoretical frequency based on the number of copies of pHT1030 enabled the role of spbB to be pinpointed.

The stability experiments performed in LB medium have shown the overall maintenance of the plasmids under nonselective conditions (FIG. 2). However, they did not enable the loss frequency of plasmids per generation to be estimated. An overnight culture in an LB medium causes the sporulation of some of the cells. When they were evaluated after about 25 generations, the values obtained for the stability of the plasmids result from a mixed population of vegetative and sporulating cells.

In order to distinguish the stability of the plasmids in the two growth states, the production of cells free from plasmids was followed separately in a rich medium (BHI) in order to prevent the triggering of sporulation and in media specific for sporulation (SP or HCT) in order to determine the frequency of production of a plasmid-free spore.

In BHI medium, the plasmids bearing the spbB locus and the entire replication region (pHT3130, pHT3120 or pHT3109) were maintained in a very stable manner, in view of the fact that more than 95% of the B. subtilis cells harbored these plasmids after 60 generations (FIG. 5A) and 99% of the B. thuringiensis cells after 80 generations (FIG. 5B). The plasmids from which spbB was missing (pHT3104a and pHT3107) and those in which the spbB gene was ruptured (pHT3108 and pHT3130ΔHpaII) were significantly less stable than the replicons bearing the entire spbB sequence (FIG. 5A and B).

A second class of plasmids (pHT3112a and pHT3113a) in which the spbA locus is absent appears to be very unstable in both B. subtilis and B. thuringiensis. However, the presence of the DNA region carrying the spbB sequence (pHT3112a) the reduces the instability, as compared with its absence (pHT3113a).

The determination of plasmid stability during sporulation was carried out by using SP and HCT media in which B. subtilis and B. thuringiensis sporulate synchronously. Just before $t_0$ of sporulation (about 15 generations after inoculation of the medium without antibiotic), the proportion of $Em^r$ cells is unchanged or only slightly reduced (FIG. 6A and B). This is in marked contrast with the results observed after complete development of the sporulation phase. The cells harboring the plasmids pHT3130ΔHpaII, pHT3108 and pHT3104a give rise to a large proportion of plasmid-free spores, in particular in B. subtilis. The plasmids pHT3130, pHT3120 and pHT3109 are maintained stably during the sporulation process. These results are in agreement with those obtained in vegetative growth and strongly suggest that during sporulation the stability of the plasmids is dependent on the DNA region carrying spbB.

After $t_0$ of sporulation there is no significant new cell growth. The instability of pHT3130ΔHpaII, pHT3108 and pHT3104a consequently result from the sporulation stage which may be considered as being a simple cell division. One of the first steps in this differentiation process is the formation of the sporulation septum which divides the cell into two unequal compartments. In both B. subtilis and B. thuringiensis the presporal compartment represents about one sixth of the volume of the parent cell (Ryter, 1965; Ribier and Lecadet, 1973). Thus, it ought to be expected that a random distribution of the plasmids would lead to a high production frequency of plasmid-free spores.

On the basis of the mean of the stability results obtained in the vegetative phase (FIG. 5A and B) or in the sporulation phase (FIG. 6A and B), the stability frequencies of the plasmids carrying the spbB locus or lacking this locus were determined and compared with the theoretical frequencies expected with a plasmid having a number of copies of 4.2 per chromosome equivalent, i.e. about 20 copies per cell prior to division (Table 1). Owing to the difficulty of extracting DNA from Bacilli at stage $t_0$ of sporulation, the plasmid copy number was not measured during this differentiation step and the hypothesis has been put forward that it is identical with that obtained during the vegetative phase.

As shown above, it appears that all of the plasmids are about 4 times less stable in B. subtilis and B. thuringiensis.

Although the calculated number of copies and the apparent behaviour of pHT3104a has been found to be similar in the two organisms, the stability difference between *B. subtilis* and *B. thuringiensis* for this type of plasmid, could result partially from errors in replication control leading to a variation in the number of copies in a population of *B. subtilis* cells. Nonetheless, other factors relating to the host must probably be considered in order to explain the considerable difference in the stability of the plasmids observed between sporulating cells of *B. subtilis* and *B. thuringiensis* (FIG. 6 and Table 1). However, in both *B. subtilis* and *B. thuringiensis* the plasmids carrying the spbB region were maintained with higher frequencies than the plasmids not carrying this region (Table 1).

Furthermore, during sporulation, the spbB$^+$ plasmids are maintained with frequencies similar to those deduced from random distribution. These results indicate that in all cases, the presence of spbB diminishes the frequency of loss of the plasmids by a factor of about 20.

Examination of the Stability Mechanism Regulated by spbB

The capacity of spbB to stabilize a heterologous replicon or to function in trans, and its effect on bacterial growth were examined in order to obtain information concerning the mechanism spbB.

In order to test the capacity of spbB to stabilize a heterologous plasmid, the vector pHT1618 was constructed by cloning the replicon pBC16Δ1 (Polak and Novick, 1982) at the SspI site of pUC18 (FIG. 7). pBC16 1 is a derivative of replicon pBC16 of *B. cereus* which confers resistance to tetracycline on Gram-positive bacteria pBC16 is a plasmid of the "rolling circle" type (Gruss and Ehrlich, 1989 Microbiol. Rev. 53:231–241).

Different DNA fragments containing the intact or interrupted spbB region were cloned into the cloning sites of pHT1618 (FIG. 7). The stability of these recombinant plasmids was analysed in *B. subtilis* during vegetative growth without antibiotic (FIG. 8). pHT1610 and pHT1611ΔHpaII were less stable than pHT1618. This reduction in stability is in agreement with the preceding data showing that the segregational stability of the plasmid pUB110, which is related to pBC16 (Polak and Novick, 1982), depends on the size and is considerably reduced by DNA insertions (Bron et al., 1988). The instability of pHT1610 clearly indicates that the AccI-BalI fragment containing the spbB gene has not conferred a stability function on the replicon.

The addition of DNA segments (ScaI-AccI or HindIII-AccI) situated upstream from the spbB gene to the plasmids completely suppressed the reduction in stability due to the cloning of the spbB gene in pHT1610. In fact, pHT1609 and pHT1611 are at least as stable as pHT1618 and significantly more stable than pHT1610 and pHT1611ΔHpaII which carry DNA insertions of similar dimensions. The determinations of the production frequency of a plasmid-free spore in an SP medium gave similar results.

Consequently, these results show that, in addition to the spbB gene, the ScaI-AccI DNA fragment situated upstream from the gene is necessary to confer stability on recombinant plasmids derived from pBC16. The deletion of the ScaI-HaeIII fragment does not diminish the stability (pHT3120) and, consequently, the essential function for stability resides in the short HaeIII-AccI fragment. This DNA segment contains the region of symmetry, a potential terminator, which may be required for the functional expression of the spbB gene product.

In order to determine whether the spbB protein is trans-acting or not, *B. subtilis* Rec$^-$ strains harboring pHT1618 or pHT1609 were transformed by the unstable plasmids pH3104a or pHT3130 HpaII. pHT1609 had no detectable effect on the stability of these two plasmids indicating that the stabilization requires that the replicon and the spbB locus are in the same molecule.

Hence spbB would appear not to be a true partition system in which the proteins function in trans in order to ensure the distribution of the plasmid to the daughter cells (Austin and Nortdström, 1990 Cell 60:351–354). This characteristic and the capacity to stabilize a heterologous replicon are analogous to those of the "killer" systems ccd and hok/sok (Jaffé et al., 1985 J. Bacterial. 163:841–849; Gerdes et al., 1986 Proc. Natl. Acad. Sci. USA 83: 3116–3120). Interestingly, the *B. subtilis* cells which harbor spbB$^+$ plasmids produce only about a third of the number of viable spores compared with those harbouring spbB$^-$ plasmids (Table 2). This is also in agreement with a model of the action of the "killer" type.

If it is supposed that, during sporulation of the *B. subtilis* cells, the high production frequency of a plasmid-free spare is equivalent with spbB$^-$ and spbB$^+$ plasmids, the apparent stability of the spbB$^+$ plasmids might consequently result from a post-segregational activity of the SpbB protein. When the spbB$^+$ plasmid is lost, the SpbB protein may become functional and its physiological effect might be to prevent or delay cellular development and the formation of viable spores.

DISCUSSION

The replication and stability functions of the Gram-positive plasmid pHT1030 were first localized on the map at a 2.9 kb BalI restriction fragment (SEQ ID NO:1)(Lereclus et al., 1988 FEMS Microbiol. Lett. 49:417–422).

The construction of the deletion derivatives of pHT1030 reveals that the minimal replicon conferring autonomous replication is included in a 1 kb DNA fragment. The plasmids carrying this DNA region show a replication behaviour similar to that of the plasmids carrying the entire BalI restriction fragment. These are plasmids with a low copy number (4.2 copies per chromosome equivalent) and they do not accumulate single-stranded DNA molecules during replication. This latter characteristic excludes a "rolling circle" mode of replicating which is found most commonly in Gram-positive replicons (Gruss and Ehrlich, 1989 Microbiol. Rev. 53:231–241).

The principal characteristic of this 1 kb DNA fragment is the absence of a sequence coding for a potential protein. Consequently, it resembles plasmids of the ColE1type which only require host proteins for their own replication. Nonetheless, unlike ColE1, the plasmids derived from pHT1030 are not amplified after addition of chloramphenicol to the culture medium These characteristics indicate that pHT1030 is located in a class of replicons which has not previously been found in the Gram-positive bacteria.

Another special characteristic of the minimal replicon of pHT1030 is a sequence (SEQ ID NO:8) of 70 nucleotides forming potentially a hairpin loop RNA structure in which one of the two complementary regions itself contains an inverted repeat sequence (SEQ ID NO:9)(mapping between the nucleotide positions 392 and 425 in FIG. 1).

The deletion of a 300 bp DNA region containing a potential promoter (which might be essential for the synthesis of the initiator RNA molecule) makes the pHT1030 derivatives incapable of replicating. This defect is suppressed by the addition co the lacZ promoter region of pUC18, but the segregational stability of the resulting plasmids (pHT3112a and pHT3113a) is seriously diminished in *B. subtilis* and *B. thuringiensis*. Consequently, this 300 bp segment defines a stability locus (spbA) probably linked to the replication function of pHT1030.

The segregational stability of the various deletion derivatives of pHT1030 was examined separately during vegetative growth and the sporulation phase The experiments indicate that the plasmids carrying the minimal replicon of pHT1030 or the plasmids deficient in the DNA region designated spbB are not maintained in a stable manner in the Bacilli, in particular in B. thuringiensis. For unknown reasons, the stability of these plasmids is worse than random in B. subtilis. Interestingly, it has been shown that the high frequency of production of a plasmid-free spore could be correlated with a random distribution of the plasmids on the basis of unequal division of the cell by the sporulation septum However, in both the vegetative phase and sporulation the plasmids carrying the spbB locus are maintained stably in the two species of Bacilli.

spbB codes for a polypeptide of 15 kDA which might be implicated in the stability of pHT1030. Once cloned in a heterologous replicon (derived from pBC16), the spbB locus confers a low but significant segregational stability, whereas an $spbB^+$ plasmid does not stabilize in trans plasmids from which spbB has been deleted or which carry an interrupted spbB gene. This indicates that the spbB locus must be linked to the replicon in order to exert its stability function.

spbB is thus actively implicated in the segregational stability of pHT1030, independently of the replication function. The mechanism by which it functions exhibits characteristics resembling those of the "killer" systems cod and hok/sok (Jaffe et al., 1985 J. Bacteriol 163:841–849; Gerdes et al., 1986 Proc Natl. Acad.Sci. USA 83:3116–3120). The plasmids carrying such loci produce a killer protein and an antagonistic agent which is a protein in the ccd system (Ogura and Hiraga, 1983 Proc Natl. Acad. Sci USA 80:4784–4788; Miki et al., 1984 J. Mol. Biol. 174:605–625), and an anti-sense RNA in the hok/sok system (Gerdes et al., 1990 Md. Microbiol.4: 1807–1818). When the plasmids are lost the blocking agent disappears more rapidly than the more stable killer determinant, permitting the expression of the killer activity which causes cell death.

The analogy between spbB and the killer mechanism is reinforced by the results obtained under conditions (sporulation in *B. subtilis*) leading to a high production frequency of spores free from plasmids. The production of viable spores is strongly reduced when the cells harbour an $spbB^+$ plasmid. This would be expected if the SpbB protein had a killer-type effect. However, no homolgy has been found between SpbB and the killer proteins CcdB and Hok, and the physiological function of SpbB has still to be characterized.

EXPERIMENTAL PROCEDURES

Bacterial Strains and Growth Conditions

The *E. coli* K-12 strain TG1 |Δ(lac-proAB) supE thi hdsD5 (F traD36 $proa^+$ pror $B^+$ lacIq lacZΔM15)| was used for the cloning and sequencing experiments. The *B. subtilis* strain 168 (trpC2) (Anagnostopoulos and Spizizen, 1961 J. Bacteriol 81:741–746) and the *B. thuringiensis* strain kurstaki HD1 cryB were used for the replication and stability assays. *E. coli, B. subtilis* and *B. thuringiensis* were transformed as described by Cohen et al. (1972 Proc Natl. Acad. Sci. USA 69:2110–2114), Anagnostopoulos and Spizizen (1961 J. Bacteriol 81:741–746) and Lereclus et al. (1989a FEMS Microbiol. Lett. 60 211–218).

A Luria broth (LB) was used for the *E. coli* cultures and preliminary stability assays with *B. subtilis* and *B. thuringiensis*. The stability of the plasmid in vegetative growth was determined in a brain-heart infusion (BHI Difco) in the case of the two Bacilli, and the stability assays during sporulation was carried out in a HCT medium (Lecadet et al., 1980 J. Gen. Microbiol. 121:203–212) in the case of *B. thuringiensis* and in an SP medium in the case of *B. subtilis*. The SP medium containing 8 g of nutrient broth (Difco) per liter, 1 mM $MgSO_4$, 13 mM KCl and 10 μM $MnCl^2$ supplemented after sterilization by 1 μM $FeSO_4$, 1 mM $CaCl_2$ and 1 g glucose The antibiotic concentrations for bacterial selection were the following: ampicillin, 100 μg/ml; erythromycin, 25 μg/ml in the case of the Bacilli and 125 μg/ml in the case of *E. coli*, and tetracycline, 10 μg/ml.

Plasmids

The plasmid pUCI8 in which the 2.9 kb BalI restriction fragment of pHT1030 (SEQ ID NO:1) was inserted at the SmaI site and the plasmid pHT1031 (Lereclus et al., 1988 FEMS Microbiol. Lett. 49:417–422) were used as DNA source to construct the various deletion derivatives of pHT1030 used in this study. These plasmids are described in FIG. 2 and FIG. 7.

The bifunctional vector pHV33 is composed of pBR322 and pC194 (Primrose and Ehrlich, 1981 Plasmid 6:193–201). pBC16Δ1 is derived from the plasmid pBC16 of B. cereus (Bernhard et al., 1978 J. Bacteriol. 133:897–903)

Stability Assays

Preliminary stability assays in an LB medium were carried out as previously described (Lereclus et al., 1988 FEMS Microbiol. Lett. 49:417–422).

The bacterial strains containing plasmids to be tested for segregational stability in vegetative growth were inoculated in the selective BHI medium and incubated overnight at 30° C. The cultures were then subsequently diluted $10^6$ fold in a BHI medium without antibiotics and incubated at 37° C. The cultures were diluted ($10^5$ to $10^6$ fold) in a fresh non-selective BHI medium every 15 to 20 generations. At regular intervals (about 20 generations) culture samples were spread on non-selective gelose dishes after suitable dilutions. About 100 colonies of each sample were spread with a tooth pick on gelose plates containing the appropriate antibiotic to determine the proportion of bacteria containing plasmids. The segregational stability of the unstable spbA-plasmids (pHT3112a and pHT3113a) was estimated by spreading samples of the recovered cultures at intervals of about 5 generations on both a selective and non-selective gelose medium after suitable dilutions.

For the stability assays during the sporulation phase overnight cultures in the selective BHI medium were diluted $10^3$ fold in a specific sporulation medium (SP or HCT) containing erythromycin (5 μg/mi) and incubated for 2 to 3 hours at 37° C. The cultures were then diluted $10^3$ fold in a fresh non-selective HCT or SP medium (zero time) and incubated at appropriate temperatures (30° C. for *B. thuringiensis* and 37° C. for *B. subtilis*). After about 15 generations (just before $t_0$ of sporulation) the samples were used to determine the fraction of cells containing plasmids as described above After 24 or 36 hours, when most of the spores have been released, the culture samples were heated at 80° C. for 10 minutes to kill the non-sporulating cells. The proportion of spores containing plasmids was then determined as above.

Determination of the Plasmid Copy Number

The plasmid copy number was determined by densitometry of photographic negatives obtained from electrophoretic gels stained with ethidium bromide The method and the parameters used for the determination of the copy number were as described by Projan et al. (1983 Plasmid 9:182–190). The size of the *B. subtilis* and *B. thuringiensis* chromosomes used to calculate the copy number was 4.2× $10^3$ kb.

Analysis of Single-stranded DNA Production Crude plasmid preparations were subjected to electrophoresis on agarose gels and transferred to nitrocellulose filters with or without denaturation (BA85, 0.45 μm, Schleicher and Schuell) as previously described by te Riele et al. (1986a EMBO J. 5: 631–637) for the *B. subtilis* cells. The filters were hybridized with pUC18 labelled with $^{32}p$.

Materials and DNA Sequencing

Restriction enzymes, T4 DNA ligase and the Klenow fragment of DNA polymerase I were supplied by New England Biolabs, Inc. The restriction enzyme Asp178 (used to cut at KpnI sites) and calf intestinal alkaline phosphatase were obtained from Boehringer Mannheim. All of the enzymes were used in accordance with the manufacturers' directions. DNA restriction fragments were purified on agarose gels using a Gene Clean kit (Bio101).

The nucleotide sequencing was carried out by the chain termination method (Sanger et al., 1977 Proc Natl. Acad. Sci. USA 74:5463–5467) using the Sequenase sequencing kit purchased from U.S. Biochemical Corp., and [alpha-$^{35}$S] -dATP (110 TBq/ mmole) supplied by Amersham Corp. Overlapping deletions were obtained according to the procedure of Dale et al. (1985 Plasmid 13:31–40) using the Cyclone system as indicated by the manufacturer (International Biotechnologies InC.).

The DNA sequence described here will appear in the EMBL library of nucleotide sequences under the entry number X59245.

In vitro transcription-translation assays were carried out with $I^{35}S/$-methionine (37 TBq/mmcie) from Amersham Corp. with the DNA EXpression System of New England Nuclear, as indicated by the supplier. Radidabelled proteins were resolved in 12.5% polyacrylamide gels (weight/ volume).

Computer Analysis

The programs were used an a Data General MV8000 computer. The DNA and amino acid sequences were analysed with the programs used at the Pasteur Institute.

TABLE 2

Effect of spbB on the sporulation of *B. subtilis*

| Plasmid | Genotype | Total number of viable spores (per ml) (a) | Percentage of Em$^r$ spores (b) |
|---|---|---|---|
| pHT3130 | spbA$^+$spbB$^+$ | $2 \times 10^{-8}$ | 96% |
| pHT3120 | spbA$^+$spbB$^+$ | $2.5 \times 10^{-8}$ | 95% |
| pHT3109 | spbA$^+$spbB$^+$ | $3 \times 10^{-8}$ | 96% |
| pHT3130ΔHpaII | spbA$^+$spbB$^-$ | $7 \times 10^{-8}$ | 18% |
| pHT3108 | spbA$^+$spbB$^-$ | $6.5 \times 10^{-8}$ | 30% |
| pHT3104a | spbA$^+$spbB$^-$ | $8 \times 10^{-8}$ | 15% |

(a) The number of viable spores was estimated by spreading dilutions of sporulating cultures on non-selective agar plates, after incubation at 80° C. for 10 minutes. The sporulating cultures were obtained in a selective SP medium.
(b) The percentage of Em$^r$ spores was estimated by repicking about 100 colonies on agar plates containing erythromycin.

2ND Example

CONSTRUCTION OF SHUTTLE VECTORS

Experimental Part and Discussion
A) Shuttle Vectors with Different Copy Numbers
  1) Removal of the HindIII site from pHT1035 pHT1035 is a 6.3 kb plasmid carrying the replication region of plasmid pHt1030 of *B. thuringiensis* (2.9 kb BalI DNA fragment (SEQ ID NO:1), a HindIII-BalI DNA fragment carrying the cat gene of pjH101 (Ferrari et al., 1983 J. Bacteriol. 154:1513–1515) and the origin of replication of pBR322 (FIG. 9) (Lereclus et al., 1988 FEMS Microbiol. Lett. 4: 417–422). The unique HindIII site of pHT1035 was removed (FIG. 9) in order to prevent any duplication of the pUC19 restriction sites (Yanisch-Perron et al., 1985 Gene 33:103–119) used for the construction of the shuttle vectors. The modification at the HindIII site does not disturb the replication and stability functions of the plasmid, since pHT1035ΔHindIII was capable of transforming *B. subtilis*

TABLE 1

Plasmid stability in the vegetative and sporulation phases

| | Generation frequency of plasmid-free cells in the vegetative phase (a) | | | Generation of plasmid-free spores in the sporulation phase (b) | | |
|---|---|---|---|---|---|---|
| Plasmid | *B. subtilis* | *B. thuringiensis* | Theoretical probability $(1/2)^{2n}$ | *B. subtilis* | *B. thuringiensis* | Theoretical probability $(5/6)^{2n}$ |
| pHT3130ΔHpaII pHT3108 pHT3104a | $7 \times 10^{-3}$ | $2 \times 10^{-3}$ | $10^{-6}$ | $8 \times 10^{-4}$ | $1.8 \times 10^{-4}$ | $2.2 \times 10^{-2}$ |
| pHT3130 pHT3120 pHT3109 | $4 \times 10^{-4}$ | $10^{-4}$ | $10^{-6}$ | $5 \times 10^{-2}$ | $<10^{-2}$ | $2.6 \times 10^{-2}$ |

(a) Frequencies determined from FIGS. 5A and 5B. The number of Em$^s$ cells at a given time divided by the corresponding number of generations. The results correspond to the mean of the data obtained with the plasmids indicated.
(b) Frequencies determined from FIGS. 6A and 6B. The generation frequence of a plasmid-free spore was estimated as the proportion of spores giving rise to Em$^s$ colonies.
(c) The theoretical probability depends on the size of the cellular compartment under consideration and the number of copies of the plasmid per cell (2n = 20).

strain 168 (Anagnostopoulos and Spizizen, 1961 J. Bacteriol. 81:741–746) in CmR (10 μg/ml) and was maintained stably without selection pressure (90% of the cells contained the plasmid after about 25 generations in a non-selective LB medium).

2) Selection of the high copy number derivative of pHT1035 HindIII.

The DNA of plasmid pHT1035 HindIII was treated with hydroxylamine (FIG. 9) and was then used to transform *E. coli* cells in order to recover plasmid DNA molecules (multimer forms) capable of transforming *B. subtilis*. Plasmids having increased numbers of copies were then selected by spreading transformed *B. subtilis* cells on a LB gelose medium containing a Cm concentration (25 µg/ml) which prevents the growth of cells harboring the law copy number plasmid pHT1035ΔHindIII (4+/−1 copies per chromosome equivalent).

Two plasmids having increased numbers of copies were selected for the continuation of the study (FIG. 9). Their copy numbers were determined by densitometry analysis of photographic negatives of agarose gels after electrophoresis using the parameters described by Projan et al. (1983, Determination of plasmid copy number by fluorescence densitometry. Plasmid 9: 182–190). The plasmids were designated pHT1035-15ΔHindIII and pHT1035-70ΔHindIII and have 15+/−5 and 70+/−20 copies, respectively, per chromosome equivalent. They are stable from the point of view of segregation given that 100% of the cells contained the plasmid after about 25 generations in a non-selective LB medium 3) Construction of the shuttle vectors It has been shown that the replication and stability regions of pHT1030 were entirely included in th 2.7 kb HpaI-BalI DNA fragment carried by pHT1035 (FIG. 9). Consequently, this DNA fragment was isolated from each of the plasmids pHT1035ΔHindIII, pHT1035-15ΔHindIII and pHT1035-70ΔHindIII and used separately to construct the plasmids pHT304, pHT315 and pHT370, respectively (FIG. 10).

These plasmids may be used in the same manner as pUC19 for cloning experiments in *E. coli*, since the fragments were inserted at the SspI site which interrupts neither the cloning sites of the polylinker nor the bla gene None of the polylinker site of pUC19 is duplicated.

These shuttle vectors were used to transform the *B. thuringiensis* strain kurstaki HD1 CryB by the electroporation procedure as described by Lereclus et al., 1989A The recombinant clones were selected on LB gelose plates containing Er (25 µg/ml). The densitometry analysis of the total DNA preparations extracted from these clones has shown that the three shuttle vectors had a copy number in *B. thuringiensis* similar to that of the corresponding parent plasmids in *B. subtilis* (FIG. 10).

B) Relationship Between the Delta-endotoxin Production and the Plasmid Copy Number.

A 3 kb HindIII restriction fragment carrying a cryIIIA gene isolated from *B. thuringiensis* strain LM79 specific for the coleoptera was subcloned into the HindIII site of each of the vectors pHT304, pHI315 and pHT370. The three resulting plasmids (pHT304ΩcryIIIA, pHT315ΩcryIIIA and pHT370ΩcryIIIA) carrying the cryIIIA gene in the same orientation, were introduced in the *B. thuringiensis* strain kurstaki HDI CryB by electroporation.

The recombinant clones were grown for 2 days at 30° C. in an HCT medium (Lecadet et al., 1980 Ber. J. Gen. Microbiol. 121: 203–212) in the presence or absence of 25 µg of Er per ml. The spore-crystal preparations harvested from the cultures were examined in a phase contrast microscope and by SDS-PAGE (sodium dodecyl sulfate polyacrylamide gel electrophoresis) (FIG. 11). The kurstaki HD1ΩCry-B recombinants harboring pHT304ΩcryIIIA did not produce detectable parasporal inclusions, whereas the cells harboring either pHT315ΩcryIIIA or pHT370ΩcryIIIA produced flat rhomboid crystals characteristic of strains active against coleopteran larvae (Herrnstadt et al., 1986 Bio/Technology 4:305–308). The major components of these crystals were two polypeptides of about 73 and 67 kDa (FIG. 11). This is in agreement with earlier results which indicated that the cryNIIIA gen of the tenebrionis strain of *B. thuringiensis* produced peptides of 73 and 67 kDa (Sekar et al., 1987). The 67 kDa component might result from proteolytic cleavage of the 73 kDa peptide. Small quantities of these peptides were found in the ssore-crystal preparations recovered from bacteria harboring pHT304•cryIIIA (FIG. 11, lane 2). This result shows that the production level of delta-endotoxin may be improved by increasing the copy number of the cry gene, at least under the experimental conditions described here However, there was no significant difference between the quantities of delta-endotoxin produced by the cells harboring pHT315ΩcryIIIA and those harboring pHT370ΩcryIIIA, thus indicating that above fifteen copies of plasmid per chromosome factors other than the number of copies of the cry gene limit the synthesis of the crystal proteins It is noted that the production of delta-endotoxins in the recombinant strains is not affected by the presence or absence of Er, suggesting that the plasmids are maintained in a stable manner in the host cells. In fact, after about 15 generations of growth followed by sporulation in an HCT medium without antibiotic, all of the spores (100%) contained the plasmid.

3D Example

Construction of a Plasmid Carrying Several (2) Genes for Delta-Endotoxins

The plasmid pHT315ΩCRYIIIA described above is digested by the enzyme SmaI, then treated with alkaline phosphatase. The linearised plasmid is then purified on an agarose gel.

The plasmid pHT408 (Lereclus et al., 1989 FEMS 60:211–218) is digested by the enzymes HpaI and SmaI. The 5 kb HpaI-SmaI restriction fragment carrying the cryA(a) gene is purified on an agarose gel and ligated in the presence of DNA ligase with the plasmid pHT315ΩCRYIIIA linearised by the enzyme SmaI. The ligation mixture is used to transform *E. coli*. The colonies which had been grown on an LB medium containing ampicillin (100% ug/ml) are replicated on a nitrocellulose filter, then hybridized with a radioactive probe (labelled with alpha $^{32}$P-dCTP) constituted by an internal region of the cryIa(a) gene. Only the clones transformed by the plasmid pHT315ΩcryIIIA carrying the cryIA(a) gene inserted at the SmaI site hybridize with the probe. The plasmid DNA of one of these dames is extracted and the restriction map of the plasmid is established in order to check the presence of the two genes cryIIIA and cryIA(a).

The resulting plasmid: pHT315ΩcryIIIΩIA(a) possesses a unique SalI restriction site which may be used to clone a third DNA fragment carrying another delta-endotoxin gene and having cohesive ends with a site cut by SalI.

Such a chimeric plasmid: pHT315ΩcryIIIΩcryIA(a) or pHT315ΩcryIIIA cryIA5(a)ΩcryX, carrying a gene conferring erythromycin resistance on Gram-positive bacteria, may be used to transform *B. thuringiensis* and thus to construct recombinant strains expressing mutiple insecticidal activities.

I claim:

1. A purified DNA fragment as shown in FIG. 2, which is selected from the group consisting of:
   (1) the BalI-AflII fragment (SEQ ID NO:5),
   (2) the BalI-ScaI fragment (SEQ ID NO:6),
   (3) the BalI-ScaI fragment with the HindIII site deleted,
   (4) the SpeI-AflII fragment (SEQ ID NO:7),
   (5) the BalI-NdeI fragment,
   (6) the BalI-SpeI fragment, and
   (7) the BalI-SspI fragment,
or which is a mutant of one of said fragments (1)–(4), wherein the mutant fragment:
   (a) has the same length as the non-mutated fragment,
   (b) hybridizes with a sequence complementary to the sequence of the non-mutated fragment under stringent conditions, and
   (c) promotes, in Gram-positive bacteria, replication of a recombinant vector within which it is inserted.

2. The purified DNA fragment of claim 1, which is the BalI-AflII fragment or said mutant of this fragment.

3. The purified DNA fragment of claim 1, which is the BalI-ScaI fragment or said mutant of this fragment.

4. The purified DNA fragment of claim 1, which is the BalI-ScaI fragment with the HindIII site deleted or said mutant of this fragment.

5. The purified DNA fragment of claim 1, which is the SpeI-AflII fragment or said mutant of this fragment.

6. The purified DNA fragment of claim 1, which is the BalI-NdeI fragment.

7. The purified DNA fragment of claim 1, which is the BalI-SpeI fragment.

8. The purified DNA fragment of claim 1, which is the BalI-SspI fragment.

9. A recombinant vector comprising:
   (A) a DNA fragment as shown in FIG. 2, which is selected from the group consisting of:
   (1) the BalI-AflII fragment (SEQ ID NO:5),
   (2) the BalI-ScaI fragment (SEQ ID NO:6),
   (3) the BalI-ScaI fragment with the HindIII site deleted,
   (4) the SpeI-AflII fragment (SEQ ID NO:7),
   (5) the BalI-NdeI fragment,
   (6) the BalI-SpeI fragment, and
   (7) the BalI-SspI fragment,
   or which is a mutant of one of said fragments (1)–(4), wherein the mutant fragment:
   (a) has the same length as the non-mutated fragment,
   (b) hybridizes with a sequence complementary to the sequence of the non-mutated fragment under stringent conditions, and
   (c) promotes, in Gram-positive bacteria, replication of a recombinant vector within which it is inserted; and
   (B) at least one nucleic acid sequence encoding a protein, which said recombinant vector does not comprise a fragment of the BalI-BalI fragment as shown in FIG. 2 other than the DNA fragment of (A).

10. The vector of claim 9, wherein (A) is the BalI-AflII fragment or said mutant of this fragment.

11. The vector of claim 9, wherein (A) is the BalI-ScaI fragment or said mutant of this fragment.

12. The vector of claim 9, wherein (A) is the BalI-ScaI fragment with the HindIII site deleted or said mutant of this fragment.

13. The vector of claim 9, wherein (A) is the SpeI-AflII fragment or said mutant of this fragment.

14. The vector of claim 9, wherein (A) is the BalI-NdeI fragment.

15. The vector of claim 9, wherein (A) is the BalI-SpeI fragment.

16. The vector of claim 9, wherein (A) is the BalI-SspI fragment.

17. The vector of claim 9, wherein (B) encodes a delta-endotoxin of *Bacillus thuringiensis* which is toxic to insect larvae, a protease, a lipase, an amylase, a protein hormone, or an antigen of bacterial, viral or parasitic origin.

18. The vector of claim 9, wherein (B) encodes a delta-endotoxin of *B. thuringiensis* which is toxic to insect larvae.

19. The vector of claim 18, wherein (B) encodes CryI, CryII, CryIII or CryIV.

20. The vector of claim 9, which is a plasmid.

21. The vector of claim 9, further comprising
   (C) a gene encoding a selectable marker.

22. The vector of claim 21, wherein said selectable marker is an enzyme necessary for the metabolism of Gram-positive bacteria.

23. The vector of claim 21, wherein said selectable marker is a protein which confers antibiotic resistance to Gram-positive bacteria expressing said protein.

24. The vector of claim 9, which is pHT3104 or pHT3105.

25. A Gram-positive bacterium transformed with a recombinant vector, wherein said vector comprises:
   (A) a DNA fragment as shown in FIG. 2, which is selected from the group consisting of:
   (1) the BalI-AflII fragment (SEQ ID NO:5),

45

(2) the BalI-ScaI fragment (SEQ ID NO:6),
(3) the BalI-ScaI fragment with the HindIII site deleted,
(4) the SpeI-AflII fragment (SEQ ID NO:7),
(5) the BalI-NdeI fragment,
(6) the BalI-SpeI fragment, and
(7) the BalI-SspI fragment, or which is a mutant of one of said fragments (1)–(4), wherein the mutant fragment:

(a) has the same length as the non-mutated fragment,
(b) hybridizes with a sequence complementary to the sequence of the non-mutated fragment under stringent conditions, and
(c) promotes, in Gram-positive bacteria, replication of a recombinant vector within which it is inserted; and (B) at least one nucleic acid sequence encoding a protein, which said recombinant vector does not comprise a fragment of the BalI-BalI fragment as shown in FIG. 2 other than the DNA fragment of (A).

26. The transformed bacterium of claim 25, wherein (A) is the BalI-AflII fragment or said mutant of this fragment.

27. The transformed bacterium of claim 25, wherein (A) is the BalI-ScaI fragment or said mutant of this fragment.

28. The transformed bacterium of claim 25, wherein (A) is the BalI-ScaI fragment with the HindIII site deleted or said mutant of this fragment.

29. The transformed bacterium of claim 25, wherein (A) is the SpeI-AflII fragment or said mutant of this fragment.

30. The transformed bacterium of claim 25, wherein (A) is the BalI-NdeI fragment.

31. The transformed bacterium of claim 25, wherein (A) is the BalI-SpeI fragment.

32. The transformed bacterium of claim 25, wherein (A) is the BalI-SspI fragment.

33. The transformed bacterium of claim 25, wherein (B) encodes a delta-endotoxin of *Bacillus thuringiensis* which is toxic to insect larvae, a protease, a lipase, an amylase, a protein hormone, or an antigen of bacterial, viral or parasitic origin.

34. The transformed bacterium of claim 25, wherein (B) encodes a delta-endotoxin of *Bacillus thuringiensis* which is toxic to insect larvae.

35. The transformed bacterium of claim 34, wherein (B) encodes CryI, CryII, CryIII or CryIV.

36. The transformed bacterium of claim 25, wherein said vector is a plasmid.

37. The transformed bacterium of claim 25, further comprising (C) a gene encoding a selectable marker.

38. The transformed bacterium of claim 37, wherein said selectable marker is an enzyme necessary for the metabolism of Gram-positive bacteria.

39. The transformed bacterium of claim 37, wherein said selectable marker is a protein which confers antibiotic resistance to Gram-positive bacteria expressing said protein.

40. The transformed bacterium of claim 25, wherein said vector is pHT3104 or pHT3105.

41. The transformed bacterium of claim 25, which is a Bacillus.

42. The transformed bacterium of claim 41, which is *Bacillus thuringiensis, Bacillus subtilis, Bacillus sphaericus* or *Bacillus megaterium*.

43. The transformed bacterium of claim 42, wherein (B) encodes a delta-endotoxin of *B. thuringiensis* which is toxic to insect larvae, a protease, a lipase, an amylase, a protein hormone, or an antigen of bacterial, viral or parasitic origin.

44. A recombinant vector comprising:

(A) a DNA fragment as shown in FIG. 2, which is selected from the group consisting of:

46

(1) the BalI-AflII fragment (SEQ ID NO:5),
(2) the BalI-ScaI fragment (SEQ ID NO:6),
(3) the BalI-ScaI fragment with the HindIII site deleted, and
(4) the SpeI-AflII fragment (SEQ ID NO:7), or which is a mutant of one of said fragments (1)–(4), wherein the mutant fragment:

(a) has the same length as the non-mutated fragment,
(b) hybridizes with a sequence complementary to the sequence of the non-mutated fragment under stringent conditions, and
(c) promotes, in Gram-positive bacteria, replication of a recombinant vector within which it is inserted; and (B) at least one nucleic acid sequence encoding a protein, which said recombinant vector does not comprise a fragment of the BalI-BalI fragment as shown in FIG. 2 other than the DNA fragment of (A), and wherein (A) is operably linked to a promoter functional in Gram-positive bacteria.

45. A Gram-positive bacterium transformed with the vector of claim 44.

46. An insecticide comprising a carrier and an amount of Gram-positive bacteria which is active against insect larvae, wherein said Gram-positive bacteria are transformed with a recombinant vector comprising:

(A) a DNA fragment as shown in FIG. 2, which is selected from the group consisting of:

(1) the BalI-AflII fragment (SEQ ID NO:5),
(2) the BalI-ScaI fragment (SEQ ID NO:6),
(3) the BalI-ScaI fragment with the HindIII site deleted,
(4) the SpeI-AflII fragment (SEQ ID NO:7),
(5) the BalI-NdeI fragment,
(6) the BalI-SpeI fragment, and
(7) the BalI-SspI fragment, or which is a mutant of one of said fragments (1)–(4), wherein the mutant fragment:

(a) has the same length as the non-mutated fragment,
(b) hybridizes with a sequence complementary to the sequence of the non-mutated fragment under stringent conditions, and
(c) promotes, in Gram-positive bacteria, replication of a recombinant vector within which it is inserted; and (B) a DNA sequence encoding an endotoxin of *B. thuringiensis* which is toxic to insect larva, which said recombinant vector does not comprise a fragment of the BalI-BalI fragment as shown in FIG. 2 other than the DNA fragment of (A).

47. The insecticide of claim 46, wherein (A) is the BalI-AflII fragment or said mutant of this fragment.

48. The insecticide of claim 46, wherein (A) is the BalI-ScaI fragment or said mutant of this fragment.

49. The insecticide of claim 46, wherein (A) is the BalI-ScaI fragment with the HindIII site deleted or said mutant of this fragment.

50. The insecticide of claim 46, wherein (A) is the SpeI-AflII fragment or said mutant of this fragment.

51. The insecticide of claim 46, wherein (A) is the BalI-NdeI fragment.

52. The insecticide of claim 47, wherein (A) is the BalI-SpeI fragment.

53. The insecticide of claim 46, wherein (A) is the BalI-SspI fragment.

54. The insecticide of claim 46, wherein (B) encodes CryI, CryII, CryIII or CryIV.

55. The insecticide of claim 46, wherein said vector is pHT3105.

47

56. The insecticide of claim 46, wherein said bacteria are Bacillus.

57. The insecticide of claim 56, wherein said bacteria are *Bacillus thuringiensis, Bacillus subtilis, Bacillus sphaericus* or *Bacillus megaterium*.

58. An isolated BstUI-BstUI DNA fragment consisting of nucleotides 1692 to 2256 of (SEQ ID NO:1), or a mutant of this fragment, wherein the mutant fragment:

(a) has the same length as the non-mutated fragment, (b) hybridizes with a sequence complementary to the sequence of the non-mutated fragment under stringent conditions, and (c) stabilizes, in Gram positive bacteria, a recombinant vector within which it is inserted.

59. The isolated DNA fragment of claim 58, which is said mutant fragment.

60. A recombinant vector comprising:

(A) a BstUI-BstUI DNA fragment consisting of nucleotides 1692 to 2256 of (SEQ ID NO:1), or a mutant of this fragment, wherein the mutant fragment:

(a) has the same length as the non-mutated fragment, (b) hybridizes with a sequence complementary to the sequence of the non-mutated fragment under stringent conditions, and (c) stabilizes, in Gram positive bacteria, a recombinant vector within which it is inserted; and (B) at least one nucleic acid sequence encoding a protein, which said recombinant vector does not comprise a fragment of the BalI-BalI fragment as shown in FIG. 2 other than the DNA fragment of (A).

61. The vector of claim 60, wherein (A) is said mutant fragment.

62. The vector of claim 60, wherein (B) encodes a delta-endotoxin of *Bacillus thuringiensis* which is toxic to insect larvae, a protease, a lipase, an amylase, a protein hormone, or an antigen of bacterial, viral or parasitic origin.

63. The vector of claim 60, wherein (B) encodes CryI, CryII, CryIII or CryIV.

64. A Gram-positive bacterium transformed with a recombinant vector comprising:

(A) a BstUI-BstUI DNA fragment consisting of nucleotides 1692 to 2256 of (SEQ ID NO:1), or a mutant of this fragment, wherein the mutant fragment:

(a) has the same length as the non-mutated fragment, (b) hybridizes with a sequence complementary to the sequence of the non-mutated fragment under stringent conditions, and

48

(c) stabilizes, in Gram positive bacteria, a recombinant vector within which it is inserted; and (B) at least one nucleic acid sequence encoding a protein, which said recombinant vector does not comprise a fragment of the BalI-BalI fragment as shown in FIG. 2 other than the DNA fragment of (A).

65. The transformed bacterium of claim 64, wherein (A) is said mutant fragment.

66. The transformed bacterium of claim 64, wherein (B) encodes a delta-endotoxin of *Bacillus thuringiensis* which is toxic to insect larvae, a protease, a lipase, an amylase, a protein hormone, or an antigen of bacterial, viral or parasitic origin.

67. The transformed bacterium of claim 64, wherein (B) encodes CryI, CryII, CryIII or CryIV.

68. The transformed bacterium of claim 64, which is a Bacillus.

69. The transformed bacterium of claim 68, which is *Bacillus thuringiensis, Bacillus subtilis, Bacillus sphaericus* or *Bacillus megaterium*.

70. An insecticide comprising a carrier and an amount of Gram-positive bacteria which is active against insect larvae, wherein said Gram-positive bacteria are transformed with a recombinant vector comprising:

(A) a BstUI-BstUI DNA fragment consisting of nucleotides 1692 to 2256 of (SEQ ID NO:1), or a mutant of this fragment, wherein the mutant fragment:

(a) has the same length as the non-mutated fragment, (b) hybridizes with a sequence complementary to the sequence of the non-mutated fragment under stringent conditions, and (c) stabilizes, in Gram positive bacteria, a recombinant vector within which it is inserted; and (B) a DNA sequence encoding an endotoxin of *B. thuringiensis* which is toxic to insect larva, which said recombinant vector does not comprise a fragment of the BalI-BalI fragment as shown in FIG. 2 other than the DNA fragment of (A).

71. The insecticide of claim 70, wherein (A) is said mutant fragment.

72. The insecticide of claim 70, wherein (B) encodes CryI, CryII, CryIII or CryIV.

73. The insecticide of claim 70, wherein said bacteria are Bacillus.

74. The insecticide of claim 73, wherein said bacteria are *Bacillus thuringiensis, Bacillus subtilis, Bacillus sphaericus* or *Bacillus megaterium*.

* * * * *

UNITED STATES PATENT AND TRADEMARK OFFICE
CERTIFICATE OF CORRECTION

PATENT NO. : 5,766,586
DATED : June 16, 1998
INVENTOR(S) : Didier LERECLUS

It is certified that error appears in the above-identified patent and that said Letters Patent is hereby corrected as shown below:

On the title page, item [22], the PCT Filing Date should be:

--[22] PCT Filed: Jul. 20, 1992--

Signed and Sealed this

Eleventh Day of April, 2000

Attest:

Q. TODD DICKINSON

Attesting Officer

Director of Patents and Trademarks

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
  ( A ) LENGTH: 2872 base pairs
  ( B ) TYPE: nucleic acid
  ( C ) STRANDEDNESS: unknown
  ( D ) TOPOLOGY: unknown ( i i ) MOLECULE TYPE: DNA (genomic)

( i x ) FEATURE:
  ( A ) NAME/KEY: misc_feature
  ( B ) LOCATION: 1789..2193
  ( D ) OTHER INFORMATION: /note= "ORF1: codes for 134 amino
   acids starting at position 2193 and terminating at
   position 1789."

( i x ) FEATURE:
  ( A ) NAME/KEY: CDS
  ( B ) LOCATION: 2521..2871

( i x ) FEATURE:
  ( A ) NAME/KEY: promoter
  ( B ) LOCATION: 75..80

( i x ) FEATURE:
  ( A ) NAME/KEY: promoter
  ( B ) LOCATION: 98..103

( x i ) SEQUENCE DESCRIPTION: SEQ ID NO:1:

```
CCATCCTCCA  AAGTTGGAGA  GTGAGTTTTA  TGTCGCAAAT  ATTAATGTTT  CTGGTGAACC      60
TTATCAAATT  TTCGTTGATT  TAATAGAAAC  ATAGCGGTAA  AATTAGCAGT  AACTTAATAG     120
AACGGAAATG  AAAAAAGCCA  CTCTCATATG  CTATTGGCTA  CCAACCTTTA  GCGAGAATGA     180
CTTAATCCTG  TACAGCCATA  CAGGACTTCG  ACTTATAAGA  GGCGCCAACC  TCAAATAAGT     240
TATTTGCCTT  GTTTTCGCGA  ACAAGGCTTA  TTAGATACAC  CTATTGTACC  GTTACTCTAC     300
GAATATTTCA  ACTAGTAATT  ACTAGCATTG  TCATATACAT  AATAAACGG   ATATAAAAGG     360
GCGTTTTCTA  TACCTAGAAG  TCTTGTAAAT  GTACAGGGCG  TTTAGATATA  GAGAACGCCC     420
TTTTTGTGTT  CCGTTCCAGT  GGAAGCTACC  ACTTAAAAA   GATGGTCTAG  TGTAGCCAAT     480
GCAGGAGAGT  ACACTCGGAT  ATCAGTTGTC  GTTGCATTCA  ACTGTCTGAC  GTAAGCGAGG     540
TAAAGGACAC  AAGCCTTGCA  TAAAACAAGC  CTACGGGATG  TAAATCCTAA  TAATGATGAT     600
AACCAAGACG  TTAGCGGCAA  AAAGTGTTGG  GGGTTCAAAA  TAAGACATGA  TTGTGCGACT     660
GGAGTTAAAC  AGTTACTCGT  AAGCGGCGAT  CATGACACTG  ATTCACGGCT  ATTCTTGTAC     720
AAGCTTTATT  ACAAGGATAT  GCGGGTTATA  TAGCGAATCA  CCCGAAAGGG  AACGGTGTTG     780
GGCGTGAGAA  ACGCACCGTA  CGGCGCAATA  CAATGCCAAT  AAGCTATATA  CGGACGGTAT     840
AGTAGTTTTG  TAAGCTATAA  CCGTTTGTCG  TCAATGCAAC  CAATCTCAAT  TCGAGACCTC     900
GGCATCTAAG  CCAGTACGAA  TGAGTGGGCG  TTTTAACCTC  GTAAATTTTC  AACAGGGGTT     960
ACTATGCCCA  AAACTACATT  CAGATTTCCT  AACAAACTCG  CCAGTATGAA  AACCTTAAGA    1020
CCTTAAAGTC  AAGGGATTTG  AAGGATTTTA  ACCTCGATTA  GCAAAAAATG  TAGAGTACTG    1080
AAGCAACTAC  CATTAACTAA  GATAGTGGGG  GATTGAGGAA  GAATCCAGAG  CTGTTTAAAT    1140
CAAGTGAAAG  ACAAGATGAA  ATTAAAAGAA  TAGTGAAAGA  TAGGGAGTG   GTTCTCTATG    1200
AGAAAGGAAA  TGGCTAGAGA  ACAAAGGCAG  CGGTTTATTG  ATCTATTGTT  AGACTTTATG    1260
```

-continued

```
GTAAAGAATC CTCATTTATT TGTTAATGGT ACAGAGGATG AAAGTAATAA TGTTGTTACA    1320
AAATGTAATA GTGATATTAA AGAGGTTGCG GAGTCATATT TAACTCTTTT ATAGTGAGAG    1380
GGTTAAAACT AATTAATATG TATTAAGGCC CAATGTTGGA ATTATTGTAT TCACTAGGC     1440
AACCTACTTA CTAAAAGTAA GATTATCCAT TAGTGGATGT TATAATATTG GGTTTTTTAA    1500
CACAATAATC ATCGCCTTTC GGTGTCGTTT GATAGAAAAG TAACCATTAG CGATGAAAAA    1560
GTCAATATAA AAAGCCATCC GTAAAAAACG GATGGCTTAC CGTACATAGG ATCGTTGGTA    1620
GGGCGGCGTA TCCTACATCT CTGGTAACTT ACCTAGCCAA TCAAATGCTT GAGAACGGCG    1680
GTTAGATAAG CGCGTGGGGA ACCTTTCCCA CCTCAAAGAT CCTATATCAT TATTATGTTA    1740
CTTTCTACAG GTAGTATACC ATGTTCTTAT ATTTAGTAA ACTCCCCGTT AGCTTAACAG     1800
GTCTTTGTAA GCAATTAAAC GTCCACTATT CAATCGTCTT GGATTTTCG CAGGACCGTT     1860
TTTTAGATCG AACATAGTTG ATAAGAACAA ATAACCGCTT GGGTCCAACT TTATAGCAAT    1920
TAGTATATGG TCATTTAAAA TCTTTACCAA TTCAACGCTA TTAGGTTCTT TAGGATTTTG    1980
CCCGACATAG TCGGGGTGTT CAACGATATC TTTTATGTGC GATGAATATT TTTCATAAAT    2040
ACCAGGATGT TGTTTCTTTA CGTGCTTTAT AAATCCGGGA ACATTTTTA CATCGTTAGA     2100
AGTGCAAGTC AAGTTATATG TATCTATAAT GATTGTGGA AGTTTGCCA CAACAGTTGG      2160
TTTATTTACA ATCTTTTTTT TATTAGCCGT CAAATTCTC CCTCATCTCG TCTCTTTATA     2220
TCTTTATTTT ATCATAAAGG AGTATTTGAA CCGTCGCGCG GGACAGGTTT ATGATAGGGA    2280
TATTTTATTG AATAATTGAT GGTATAAGGG ACTTCATGC TTGGAAAGTG GGGATTATGA     2340
ATTAGATGCT TGTCCACAAT ATGTTCCAAT GTAATTAAAA TTTATGTTCC CACCTTGACC    2400
AAACATCACG TCCATACTTA AATCGTCCCT CCTTTAATAG GTAAATATT AATTTACCTT     2460
AATAAAAAAA TAATGGATAA TAGTATTCGT CTGAATTTAT ATAATCAGGG GGAACTATTG    2520
```

```
ATG CTG GGG ATA CTA TTT ACA GCG GCG CCA TCT ACT GAT GTC GTA AAG     2568
Met Leu Gly Ile Leu Phe Thr Ala Ala Pro Ser Thr Asp Val Val Lys
 1               5                  10                  15

GAT TTG CAA GAT AAA GTT ATA TCA TTG CAG GAT CAT GAG GTA GCG TTT     2616
Asp Leu Gln Asp Lys Val Ile Ser Leu Gln Asp His Glu Val Ala Phe
             20                  25                  30

TTG AAC ACC ACG ATA TCT AAT ATG TTA ACA GCA GTA GGT ATT GGA GTG     2664
Leu Asn Thr Thr Ile Ser Asn Met Leu Thr Ala Val Gly Ile Gly Val
         35                  40                  45

GCA ATT ATA ACG GCG GTT TTT ACA GCA GCG TTT GCT TAT GTT ACA TAT     2712
Ala Ile Ile Thr Ala Val Phe Thr Ala Ala Phe Ala Tyr Val Thr Tyr
     50                  55                  60

TCT AAT AAG CGT GCT AAA AAG AAT ATG GAC GAG GCT AGT AGA AAA TTA     2760
Ser Asn Lys Arg Ala Lys Lys Asn Met Asp Glu Ala Ser Arg Lys Leu
 65                  70                  75                  80

GAA GAA GCA GAA AGT AAA GTT TCT GTG CTA GAG GAG AAA AGC GCT CAA     2808
Glu Glu Ala Glu Ser Lys Val Ser Val Leu Glu Glu Lys Ser Ala Gln
                 85                  90                  95

TTG GAG AGG AAG ATT CTT GAA GCT GAA CAA CTC TTA GCT GAT GCC AAT     2856
Leu Glu Arg Lys Ile Leu Glu Ala Glu Gln Leu Leu Ala Asp Ala Asn
            100                 105                 110

TCT ATT TCT AAT GTG G                                                2872
Ser Ile Ser Asn Val
            115
```

( 2 ) INFORMATION FOR SEQ ID NO:2:

( i ) SEQUENCE CHARACTERISTICS:

( A ) LENGTH: 117 amino acids (B) TYPE: amino acid
(D) TOPOLOGY: linear (ii) MOLECULE TYPE: protein (xi) SEQUENCE DESCRIPTION: SEQ ID NO:2:

| Met | Leu | Gly | Ile | Leu | Phe | Thr | Ala | Ala | Pro | Ser | Thr | Asp | Val | Val | Lys |
|---|---|---|---|---|---|---|---|---|---|---|---|---|---|---|---|
| 1 | | | | 5 | | | | | 10 | | | | | 15 | |
| Asp | Leu | Gln | Asp | Lys | Val | Ile | Ser | Leu | Gln | Asp | His | Glu | Val | Ala | Phe |
| | | | 20 | | | | | 25 | | | | | 30 | | |
| Leu | Asn | Thr | Thr | Ile | Ser | Asn | Met | Leu | Thr | Ala | Val | Gly | Ile | Gly | Val |
| | | | 35 | | | | 40 | | | | | 45 | | | |
| Ala | Ile | Ile | Thr | Ala | Val | Phe | Thr | Ala | Ala | Phe | Ala | Tyr | Val | Thr | Tyr |
| | | 50 | | | | 55 | | | | | 60 | | | | |
| Ser | Asn | Lys | Arg | Ala | Lys | Lys | Asn | Met | Asp | Glu | Ala | Ser | Arg | Lys | Leu |
| 65 | | | | | 70 | | | | 75 | | | | | | 80 |
| Glu | Glu | Ala | Glu | Ser | Lys | Val | Ser | Val | Leu | Glu | Glu | Lys | Ser | Ala | Gln |
| | | | | 85 | | | | | 90 | | | | | 95 | |
| Leu | Glu | Arg | Lys | Ile | Leu | Glu | Ala | Glu | Gln | Leu | Leu | Ala | Asp | Ala | Asn |
| | | | 100 | | | | | 105 | | | | | 110 | | |
| Ser | Ile | Ser | Asn | Val |
| | | | | 115 |

(2) INFORMATION FOR SEQ ID NO:3:

(i) SEQUENCE CHARACTERISTICS:
(A) LENGTH: 134 amino acids
(B) TYPE: amino acid
(C) STRANDEDNESS: Not Relevant
(D) TOPOLOGY: unknown (ii) MOLECULE TYPE: peptide (xi) SEQUENCE DESCRIPTION: SEQ ID NO:3:

| Met | Thr | Ala | Asn | Lys | Lys | Lys | Ile | Val | Asn | Lys | Pro | Thr | Val | Val | Ala |
|---|---|---|---|---|---|---|---|---|---|---|---|---|---|---|---|
| 1 | | | | 5 | | | | | 10 | | | | | 15 | |
| Lys | Leu | Pro | Gln | Ile | Ile | Ile | Asp | Thr | Tyr | Asn | Leu | Thr | Cys | Thr | Ser |
| | | | 20 | | | | | 25 | | | | | 30 | | |
| Asn | Asp | Val | Lys | Met | Phe | Pro | Gly | Phe | Ile | Lys | His | Val | Lys | Lys | Gln |
| | | | 35 | | | | | 40 | | | | | 45 | | |
| His | Pro | Gly | Ile | Tyr | Glu | Lys | Tyr | Ser | Ser | His | Ile | Lys | Asp | Ile | Val |
| | | | 50 | | | | | 55 | | | | | 60 | | |
| Glu | His | Pro | Asp | Tyr | Val | Gly | Gln | Asn | Pro | Lys | Glu | Pro | Asn | Ser | Val |
| 65 | | | | | 70 | | | | | 75 | | | | | 80 |
| Glu | Leu | Val | Lys | Ile | Leu | Asn | Asp | His | Ile | Leu | Ile | Ala | Ile | Lys | Leu |
| | | | | 85 | | | | | 90 | | | | | 95 | |
| Asp | Pro | Ser | Gly | Tyr | Leu | Phe | Leu | Ser | Thr | Met | Phe | Asp | Leu | Lys | Asn |
| | | | 100 | | | | | 105 | | | | | 110 | | |
| Gly | Pro | Ala | Lys | Ile | Gln | Arg | Arg | Leu | Asn | Ser | Gly | Arg | Leu | Ile | Ala |
| | | | 115 | | | | | 120 | | | | | 125 | | |
| Tyr | Lys | Asp | Leu | Leu | Ser |
| | | 130 | | | |

(2) INFORMATION FOR SEQ ID NO:4:

(i) SEQUENCE CHARACTERISTICS:
(A) LENGTH: 2642 base pairs
(B) TYPE: nucleic acid
(C) STRANDEDNESS: unknown
(D) TOPOLOGY: unknown -continued ( i i ) MOLECULE TYPE: DNA (genomic)

( i x ) FEATURE:
    ( A ) NAME/KEY: promoter
    ( B ) LOCATION: 75..80

( i x ) FEATURE:
    ( A ) NAME/KEY: promoter
    ( B ) LOCATION: 98..103

( x i ) SEQUENCE DESCRIPTION: SEQ ID NO:4:

```
CCATCCTCCA  AAGTTGGAGA  GTGAGTTTTA  TGTCGCAAAT  ATTAATGTTT  CTGGTGAACC    60
TTATCAAATT  TTCGTTGATT  TAATAGAAAC  ATAGCGGTAA  AATTAGCAGT  AACTTAATAG   120
AACGGAAATG  AAAAAGCCA   CTCTCATATG  CTATTGGCTA  CCAACCTTTA  GCGAGAATGA   180
CTTAATCCTG  TACAGCCATA  CAGGACTTCG  ACTTATAAGA  GGCGCCAACC  TCAAATAAGT   240
TATTTGCCTT  GTTTTCGCGA  ACAAGGCTTA  TTAGATACAC  CTATTGTACC  GTTACTCTAC   300
GAATATTTCA  ACTAGTAATT  ACTAGCATTG  TCATATACAT  AATAAACGG   ATATAAAGG    360
GCGTTTTCTA  TACCTAGAAG  TCTTGTAAAT  GTACAGGGCG  TTTAGATATA  GAGAACGCCC   420
TTTTTGTGTT  CCGTTCCAGT  GGAAGCTACC  ACTTAAAAA   GATGGTCTAG  TGTAGCCAAT   480
GCAGGAGAGT  ACACTCGGAT  ATCAGTTGTC  GTTGCATTCA  ACTGTCTGAC  GTAAGCGAGG   540
TAAAGGACAC  AAGCCTTGCA  TAAAACAAGC  CTACGGGATG  TAAATCCTAA  TAATGATGAT   600
AACCAAGACG  TTAGCGGCAA  AAAGTGTTGG  GGGTTCAAAA  TAAGACATGA  TTGTGCGACT   660
GGAGTTAAAC  AGTTACTCGT  AAGCGGCGAT  CATGACACTG  ATTCACGGCT  ATTCTTGTAC   720
AAGCTTTATT  ACAAGGATAT  GCGGGTTATA  TAGCGAATCA  CCCGAAAGGG  AACGGTGTTG   780
GGCGTGAGAA  ACGCACCGTA  CGGCGCAATA  CAATGCCAAT  AAGCTATATA  CGGACGGTAT   840
AGTAGTTTTG  TAAGCTATAA  CCGTTTGTCG  TCAATGCAAC  CAATCTCAAT  TCGAGACCTC   900
GGCATCTAAG  CCAGTACGAA  TGAGTGGGCG  TTTTAACCTC  GTAAATTTTC  AACAGGGGTT   960
ACTATGCCCA  AAACTACATT  CAGATTTCCT  AACAAACTCG  CCAGTATGAA  AACCTTAAGA  1020
CCTTAAAGTC  AAGGGATTTG  AAGGATTTTA  ACCTCGATTA  GCAAAAATG   TAGAGTACTG  1080
AAGCAACTAC  CATTAACTAA  GATAGTGGGG  GATTGAGGAA  GAATCCAGAG  CTGTTTAAAT  1140
CAAGTGAAAG  ACAAGATGAA  ATTAAAAGAA  TAGTGAAAGA  TAGGGGAGTG  GTTCTCTATG  1200
AGAAAGGAAA  TGGCTAGAGA  ACAAAGGCAG  CGGTTTATTG  ATCTATTGTT  AGACTTTATG  1260
GTAAAGAATC  CTCATTTATT  TGTTAATGGT  ACAGAGGATG  AAAGTAATAA  TGTTGTTACA  1320
AAATGTAATA  GTGATATTAA  AGAGGTTGCG  GAGTCATATT  TAACTCTTTT  ATAGTGAGAG  1380
GGTTAAAACT  AATTAATATG  TATTAAGGCC  CAATGTTGGA  ATTATTGTAT  TCACTAGGC   1440
AACCTACTTA  CTAAAAGTAA  GATTATCCAT  TAGTGGATGT  TATAATATTG  GGTTTTTTAA  1500
CACAATAATC  ATCGCCTTTC  GGTGTCGTTT  GATAGAAAAG  TAACCATTAG  CGATGAAAAA  1560
GTCAATATAA  AAAGCCATCC  GTAAAAAACG  GATGGCTTAC  CGTACATAGG  ATCGTTGGTA  1620
GGGCGGCGTA  TCCTACATCT  CTGGTAACTT  ACCTAGCCAA  TCAAATGCTT  GAGAACGGCG  1680
GTTAGATAAG  CGCGTGGGGA  ACCTTTCCCA  CCTCAAAGAT  CCTATATCAT  TATTATGTTA  1740
CTTTCTACAG  GTAGTATACC  ATGTTCTTAT  ATTTTAGTAA  ACTCCCCGTT  AGCTTAACAG  1800
GTCTTTGTAA  GCAATTAAAC  GTCCACTATT  CAATCGTCTT  TGGATTTTCG  CAGGACCGTT  1860
TTTTAGATCG  AACATAGTTG  ATAAGAACAA  ATAACCGCTT  GGGTCCAACT  TTATAGCAAT  1920
TAGTATATGG  TCATTTAAAA  TCTTTACCAA  TTCAACGCTA  TTAGGTTCTT  TAGGATTTTG  1980
CCCGACATAG  TCGGGGTGTT  CAACGATATC  TTTTATGTGC  GATGAATATT  TTTCATAAAT  2040
```

-continued

| | | | | | |
|---|---|---|---|---|---|
| ACCAGGATGT | TGTTTCTTTA | CGTGCTTTAT | AAATCCGGGA | AACATTTTTA | CATCGTTAGA | 2100
| AGTGCAAGTC | AAGTTATATG | TATCTATAAT | GATTTGTGGA | AGTTTTGCCA | CAACAGTTGG | 2160
| TTTATTTACA | ATCTTTTTTT | TATTAGCCGT | CAAATTTCTC | CCTCATCTCG | TCTCTTTATA | 2220
| TCTTTATTTT | ATCATAAAGG | AGTATTTGAA | CCGTCGCGCG | GGACAGGTTT | ATGATAGGGA | 2280
| TATTTTATTG | AATAATTGAT | GGTATAAGGG | ACTTCATGC | TTGGAAAGTG | GGGATTATGA | 2340
| ATTAGATGCT | TGTCCACAAT | ATGTTCCAAT | GTAATTAAAA | TTTATGTTCC | CACCTTGACC | 2400
| AAACATCACG | TCCATACTTA | AATCGTCCCT | CCTTTAATAG | GTAAATATT | AATTTACCTT | 2460
| AATAAAAAAA | TAATGGATAA | TAGTATTCGT | CTGAATTTAT | ATAATCAGGG | GGAACTATTG | 2520
| ATGCTGGGGA | TACTATTTAC | AGCGGCGCCA | TCTACTGATG | TCGTAAAGGA | TTTGCAAGAT | 2580
| AAAGTTATAT | CATTGCAGGA | TCATGAGGTA | GCGTTTTGA | ACACCACGAT | ATCTAATATG | 2640
| TT | | | | | | 2642

(2) INFORMATION FOR SEQ ID NO:5:

(i) SEQUENCE CHARACTERISTICS:
  (A) LENGTH: 1016 base pairs
  (B) TYPE: nucleic acid
  (C) STRANDEDNESS: unknown
  (D) TOPOLOGY: unknown (ii) MOLECULE TYPE: DNA (genomic)

(xi) SEQUENCE DESCRIPTION: SEQ ID NO:5:

| | | | | | |
|---|---|---|---|---|---|
| CCATCCTCCA | AAGTTGGAGA | GTGAGTTTTA | TGTCGCAAAT | ATTAATGTTT | CTGGTGAACC | 60
| TTATCAAATT | TTCGTTGATT | TAATAGAAAC | ATAGCGGTAA | AATTAGCAGT | AACTTAATAG | 120
| AACGGAAATG | AAAAAAGCCA | CTCTCATATG | CTATTGGCTA | CCAACCTTTA | GCGAGAATGA | 180
| CTTAATCCTG | TACAGCCATA | CAGGACTTCG | ACTTATAAGA | GGCGCCAACC | TCAAATAAGT | 240
| TATTTGCCTT | GTTTTCGCGA | ACAAGGCTTA | TTAGATACAC | CTATTGTACC | GTTACTCTAC | 300
| GAATATTTCA | ACTAGTAATT | ACTAGCATTG | TCATATACAT | AATAAAACGG | ATATAAAAGG | 360
| GCGTTTTCTA | TACCTAGAAG | TCTTGTAAAT | GTACAGGGCG | TTTAGATATA | GAACGCCC | 420
| TTTTTGTGTT | CCGTTCCAGT | GGAAGCTACC | ACTTTAAAAA | GATGGTCTAG | TGTAGCCAAT | 480
| GCAGGAGAGT | ACACTCGGAT | ATCAGTTGTC | GTTGCATTCA | ACTGTCTGAC | GTAAGCGAGG | 540
| TAAAGGACAC | AAGCCTTGCA | TAAAACAAGC | CTACGGGATG | TAAATCCTAA | TAATGATGAT | 600
| AACCAAGACG | TTAGCGGCAA | AAAGTGTTGG | GGGTTCAAAA | TAAGACATGA | TTGTGCGACT | 660
| GGAGTTAAAC | AGTTACTCGT | AAGCGGCGAT | CATGACACTG | ATTCACGGCT | ATTCTTGTAC | 720
| AAGCTTTATT | ACAAGGATAT | GCGGGTTATA | TAGCGAATCA | CCCGAAAGGG | AACGGTGTTG | 780
| GGCGTGAGAA | ACGCACCGTA | CGGCGCAATA | CAATGCCAAT | AAGCTATATA | CGGACGGTAT | 840
| AGTAGTTTTG | TAAGCTATAA | CCGTTTGTCG | TCAATGCAAC | CAATCTCAAT | TCGAGACCTC | 900
| GGCATCTAAG | CCAGTACGAA | TGAGTGGGCG | TTTTAACCTC | GTAAATTTTC | AACAGGGGTT | 960
| ACTATGCCCA | AAACTACATT | CAGATTTCCT | AACAAACTCG | CCAGTATGAA | AACCTT | 1016

(2) INFORMATION FOR SEQ ID NO:6:

(i) SEQUENCE CHARACTERISTICS:
  (A) LENGTH: 1076 base pairs
  (B) TYPE: nucleic acid
  (C) STRANDEDNESS: unknown
  (D) TOPOLOGY: unknown (ii) MOLECULE TYPE: DNA (genomic)

( x i ) SEQUENCE DESCRIPTION: SEQ ID NO:6:

| | | | | | | |
|---|---|---|---|---|---|---|
| CCATCCTCCA | AAGTTGGAGA | GTGAGTTTTA | TGTCGCAAAT | ATTAATGTTT | CTGGTGAACC | 60 |
| TTATCAAATT | TTCGTTGATT | TAATAGAAAC | ATAGCGGTAA | AATTAGCAGT | AACTTAATAG | 120 |
| AACGGAAATG | AAAAAGCCA | CTCTCATATG | CTATTGGCTA | CCAACCTTTA | GCGAGAATGA | 180 |
| CTTAATCCTG | TACAGCCATA | CAGGACTTCG | ACTTATAAGA | GGCGCCAACC | TCAAATAAGT | 240 |
| TATTTGCCTT | GTTTCGCGA | ACAAGGCTTA | TTAGATACAC | CTATTGTACC | GTTACTCTAC | 300 |
| GAATATTTCA | ACTAGTAATT | ACTAGCATTG | TCATATACAT | AATAAAACGG | ATATAAAAGG | 360 |
| GCGTTTTCTA | TACCTAGAAG | TCTTGTAAAT | GTACAGGGCG | TTTAGATATA | GAGAACGCCC | 420 |
| TTTTTGTGTT | CCGTTCCAGT | GGAAGCTACC | ACTTTAAAAA | GATGGTCTAG | TGTAGCCAAT | 480 |
| GCAGGAGAGT | ACACTCGGAT | ATCAGTTGTC | GTTGCATTCA | ACTGTCTGAC | GTAAGCGAGG | 540 |
| TAAAGGACAC | AAGCCTTGCA | TAAAACAAGC | CTACGGGATG | TAAATCCTAA | TAATGATGAT | 600 |
| AACCAAGACG | TTAGCGGCAA | AAAGTGTTGG | GGGTTCAAAA | TAAGACATGA | TTGTGCGACT | 660 |
| GGAGTTAAAC | AGTTACTCGT | AAGCGGCGAT | CATGACACTG | ATTCACGGCT | ATTCTTGTAC | 720 |
| AAGCTTTATT | ACAAGGATAT | GCGGGTTATA | TAGCGAATCA | CCCGAAAGGG | AACGGTGTTG | 780 |
| GGCGTGAGAA | ACGCACCGTA | CGGCGCAATA | CAATGCCAAT | AAGCTATATA | CGGACGGTAT | 840 |
| AGTAGTTTTG | TAAGCTATAA | CCGTTTGTCG | TCAATGCAAC | CAATCTCAAT | TCGAGACCTC | 900 |
| GGCATCTAAG | CCAGTACGAA | TGAGTGGGCG | TTTTAACCTC | GTAAATTTTC | AACAGGGGTT | 960 |
| ACTATGCCCA | AAACTACATT | CAGATTTCCT | AACAAACTCG | CCAGTATGAA | AACCTTAAGA | 1020 |
| CCTTAAAGTC | AAGGGATTTG | AAGGATTTTA | ACCTCGATTA | GCAAAAATG | TAGAGT | 1076 |

( 2 ) INFORMATION FOR SEQ ID NO:7:

( i ) SEQUENCE CHARACTERISTICS:
        ( A ) LENGTH: 705 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:7:

| | | | | | | |
|---|---|---|---|---|---|---|
| CTAGTAATTA | CTAGCATTGT | CATATACATA | ATAAAACGGA | TATAAAAGGG | CGTTTTCTAT | 60 |
| ACCTAGAAGT | CTTGTAAATG | TACAGGGCGT | TTAGATATAG | AGAACGCCCT | TTTTGTGTTC | 120 |
| CGTTCCAGTG | GAAGCTACCA | CTTTAAAAAG | ATGGTCTAGT | GTAGCCAATG | CAGGAGAGTA | 180 |
| CACTCGGATA | TCAGTTGTCG | TTGCATTCAA | CTGTCTGACG | TAAGCGAGGT | AAAGGACACA | 240 |
| AGCCTTGCAT | AAAACAAGCC | TACGGGATGT | AAATCCTAAT | AATGATGATA | CCAAGACGT | 300 |
| TAGCGGCAAA | AAGTGTTGGG | GGTTCAAAAT | AAGACATGAT | TGTGCGACTG | GAGTTAAACA | 360 |
| GTTACTCGTA | AGCGGCGATC | ATGACACTGA | TTCACGGCTA | TTCTTGTACA | AGCTTTATTA | 420 |
| CAAGGATATG | CGGGTTATAT | AGCGAATCAC | CCGAAAGGGA | ACGGTGTTGG | GCGTGAGAAA | 480 |
| CGCACCGTAC | GGCGCAATAC | AATGCCAATA | AGCTATATAC | GGACGGTATA | GTAGTTTTGT | 540 |
| AAGCTATAAC | CGTTTGTCGT | CAATGCAACC | AATCTCAATT | CGAGACCTCG | GCATCTAAGC | 600 |
| CAGTACGAAT | GAGTGGGCGT | TTAACCTCG | TAAATTTTCA | ACAGGGGTTA | CTATGCCCAA | 660 |
| AACTACATTC | AGATTTCCTA | ACAAACTCGC | CAGTATGAAA | ACCTT | | 705 |

( 2 ) INFORMATION FOR SEQ ID NO:8:

( i ) SEQUENCE CHARACTERISTICS:
        ( A ) LENGTH: 70 base pairs ( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:8:

| AAAAGGGCGT | TTTCTATACC | TAGAAGTCTT | GTAAATGTAC | AGGGCGTTTA | GATATAGAGA | 60 |
|---|---|---|---|---|---|---|
| ACGCCCTTTT | | | | | | 70 |

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:9:

| AGGGCGTTTA | GATATAGAGA | ACGCCCT | 27 |
|---|---|---|---|

( 2 ) INFORMATION FOR SEQ ID NO:10:

( i ) SEQUENCE CHARACTERISTICS:
        ( A ) LENGTH: 146 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:10:

| CCATCCTCCA | AAGTTGGAGA | GTGAGTTTTA | TGTCGCAAAT | ATTAATGTTT | CTGGTGAACC | 60 |
|---|---|---|---|---|---|---|
| TTATCAAATT | TTCGTTGATT | TAATAGAAAC | ATAGCGGTAA | AATTAGCAGT | AACTTAATAG | 120 |
| AACGGAAATG | AAAAAAGCCA | CTCTCA | | | | 146 |

( 2 ) INFORMATION FOR SEQ ID NO:11:

( i ) SEQUENCE CHARACTERISTICS:
        ( A ) LENGTH: 304 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:11:

| CCATCCTCCA | AAGTTGGAGA | GTGAGTTTTA | TGTCGCAAAT | ATTAATGTTT | CTGGTGAACC | 60 |
|---|---|---|---|---|---|---|
| TTATCAAATT | TTCGTTGATT | TAATAGAAAC | ATAGCGGTAA | AATTAGCAGT | AACTTAATAG | 120 |
| AACGGAAATG | AAAAAAGCCA | CTCTCATATG | CTATTGGCTA | CCAACCTTTA | GCGAGAATGA | 180 |
| CTTAATCCTG | TACAGCCATA | CAGGACTTCG | ACTTATAAGA | GGCGCCAACC | TCAAATAAGT | 240 |
| TATTTGCCTT | GTTTTCGCGA | ACAAGGCTTA | TTAGATACAC | CTATTGTACC | GTTACTCTAC | 300 |
| GAAT | | | | | | 304 |

( 2 ) INFORMATION FOR SEQ ID NO:12:

( i ) SEQUENCE CHARACTERISTICS:
        ( A ) LENGTH: 314 base pairs
        ( B ) TYPE: nucleic acid
        ( C ) STRANDEDNESS: unknown
        ( D ) TOPOLOGY: unknown (i) MOLECULE TYPE: DNA (genomic)

(xi) SEQUENCE DESCRIPTION: SEQ ID NO:12:

```
CCATCCTCCA AAGTTGGAGA GTGAGTTTTA TGTCGCAAAT ATTAATGTTT CTGGTGAACC        60
TTATCAAATT TTCGTTGATT TAATAGAAAC ATAGCGGTAA AATTAGCAGT AACTTAATAG       120
AACGGAAATG AAAAAGCCA CTCTCATATG CTATTGGCTA CCAACCTTTA GCGAGAATGA        180
CTTAATCCTG TACAGCCATA CAGGACTTCG ACTTATAAGA GGCGCCAACC TCAAATAAGT       240
TATTTGCCTT GTTTTCGCGA ACAAGGCTTA TTAGATACAC CTATTGTACC GTTACTCTAC       300
GAATATTTCA ACTA                                                         314
```

(2) INFORMATION FOR SEQ ID NO:13:

(i) SEQUENCE CHARACTERISTICS:
    (A) LENGTH: 1235 base pairs
    (B) TYPE: nucleic acid
    (C) STRANDEDNESS: unknown
    (D) TOPOLOGY: unknown (i) MOLECULE TYPE: DNA (genomic)

(xi) SEQUENCE DESCRIPTION: SEQ ID NO:13:

```
GCCCAATGTT GGAATTATTG TATTTCACTA GGCAACCTAC TTACTAAAAG TAAGATTATC        60
CATTAGTGGA TGTTATAATA TTGGGTTTTT TAACACAATA ATCATCGCCT TTCGGTGTCG       120
TTTGATAGAA AAGTAACCAT TAGCGATGAA AAAGTCAATA TAAAAAGCCA TCCGTAAAAA       180
ACGGATGGCT TACCGTACAT AGGATCGTTG GTAGGCGGC GTATCCTACA TCTCTGGTAA        240
CTTACCTAGC CAATCAAATG CTTGAGAACG GCGGTTAGAT AAGCGCGTGG GGAACCTTTC       300
CCACCTCAAA GATCCTATAT CATTATTATG TTACTTTCTA CAGGTAGTAT ACCATGTTCT       360
TATATTTTAG TAAACTCCCC GTTAGCTTAA CAGGTCTTTG TAAGCAATTA AACGTCCACT       420
ATTCAATCGT CTTTGGATTT TCGCAGGACC GTTTTTAGA TCGAACATAG TTGATAAGAA        480
CAAATAACCG CTTGGGTCCA ACTTTATAGC AATTAGTATA TGGTCATTTA AAATCTTTAC       540
CAATTCAACG CTATTAGGTT CTTTAGGATT TTGCCCGACA TAGTCGGGGT GTTCAACGAT       600
ATCTTTTATG TGCGATGAAT ATTTTTCATA AATACCAGGA TGTTGTTTCT TTACGTGCTT       660
TATAAATCCG GGAAACATTT TTACATCGTT AGAAGTGCAA GTCAAGTTAT ATGTATCTAT       720
AATGATTTGT GGAAGTTTTG CCACAACAGT TGGTTTATTT ACAATCTTTT TTTTATTAGC       780
CGTCAAATTT CTCCCTCATC TCGTCTCTTT ATATCTTTAT TTTATCATAA AGGAGTATTT       840
GAACCGTCGC GCGGGACAGG TTTATGATAG GGATATTTTA TTGAATAATT GATGGTATAA       900
GGGACTTTCA TGCTTGGAAA GTGGGGATTA TGAATTAGAT GCTTGTCCAC AATATGTTCC       960
AATGTAATTA AAATTTATGT TCCCACCTTG ACCAAACATC ACGTCCATAC TTAAATCGTC      1020
CCTCCTTTAA TAGGTAAAAT ATTAATTTAC CTTAATAAAA AATAATGGA TAATAGTATT       1080
CGTCTGAATT TATATAATCA GGGGGAACTA TTGATGCTGG GGATACTATT TACAGCGGCG      1140
CCATCTACTG ATGTCGTAAA GGATTTGCAA GATAAAGTTA TATCATTGCA GGATCATGAG      1200
GTAGCGTTTT TGAACACCAC GATATCTAAT ATGTT                                 1235
```

(2) INFORMATION FOR SEQ ID NO:14:

(i) SEQUENCE CHARACTERISTICS:
    (A) LENGTH: 2870 base pairs
    (B) TYPE: nucleic acid
    (C) STRANDEDNESS: unknown
    (D) TOPOLOGY: unknown ( i i ) MOLECULE TYPE: DNA (genomic)

( x i ) SEQUENCE DESCRIPTION: SEQ ID NO:14:

| | | | | | | |
|---|---|---|---|---|---|---|
| CCATCCTCCA | AAGTTGGAGA | GTGAGTTTTA | TGTCGCAAAT | ATTAATGTTT | CTGGTGAACC | 60 |
| TTATCAAATT | TTCGTTGATT | TAATAGAAAC | ATAGCGGTAA | AATTAGCAGT | AACTTAATAG | 120 |
| AACGGAAATG | AAAAAGCCA | CTCTCATATG | CTATTGGCTA | CCAACCTTTA | GCGAGAATGA | 180 |
| CTTAATCCTG | TACAGCCATA | CAGGACTTCG | ACTTATAAGA | GGCGCCAACC | TCAAATAAGT | 240 |
| TATTTGCCTT | GTTTCGCGA | ACAAGGCTTA | TTAGATACAC | CTATTGTACC | GTTACTCTAC | 300 |
| GAATATTTCA | ACTAGTAATT | ACTAGCATTG | TCATATACAT | AATAAACGG | ATATAAAGG | 360 |
| GCGTTTTCTA | TACCTAGAAG | TCTTGTAAAT | GTACAGGGCG | TTAGATATA | GAACGCCC | 420 |
| TTTTGTGTT | CCGTTCCAGT | GGAAGCTACC | ACTTAAAAA | GATGGTCTAG | TGTAGCCAAT | 480 |
| GCAGGAGAGT | ACACTCGGAT | ATCAGTTGTC | GTTGCATTCA | ACTGTCTGAC | GTAAGCGAGG | 540 |
| TAAAGGACAC | AAGCCTTGCA | TAAAACAAGC | CTACGGGATG | TAAATCCTAA | TAATGATGAT | 600 |
| AACCAAGACG | TTAGCGGCAA | AAAGTGTTGG | GGGTTCAAAA | TAAGACATGA | TTGTGCGACT | 660 |
| GGAGTTAAAC | AGTTACTCGT | AAGCGGCGAT | CATGACACTG | ATTCACGGCT | ATTCTTGTAC | 720 |
| AAGCTTTATT | ACAAGGATAT | GCGGGTTATA | TAGCGAATCA | CCCGAAAGGG | AACGGTGTTG | 780 |
| GGCGTGAGAA | ACGCACCGTA | CGGCGCAATA | CAATGCCAAT | AAGCTATATA | CGGACGGTAT | 840 |
| AGTAGTTTTG | TAAGCTATAA | CCGTTTGTCG | TCAATGCAAC | CAATCTCAAT | TCGAGACCTC | 900 |
| GGCATCTAAG | CCAGTACGAA | TGAGTGGGCG | TTTTAACCTC | GTAAATTTTC | AACAGGGGTT | 960 |
| ACTATGCCCA | AAACTACATT | CAGATTTCCT | AACAAACTCG | CCAGTATGAA | AACCTTAAGA | 1020 |
| CCTTAAAGTC | AAGGGATTTG | AAGGATTTTA | ACCTCGATTA | GCAAAAATG | TAGAGTACTG | 1080 |
| AAGCAACTAC | CATTAACTAA | GATAGTGGGG | GATTGAGGAA | GAATCCAGAG | CTGTTTAAAT | 1140 |
| CAAGTGAAAG | ACAAGATGAA | ATTAAAAGAA | TAGTGAAAGA | TAGGGGAGTG | GTTCTCTATG | 1200 |
| AGAAAGGAAA | TGGCTAGAGA | ACAAAGGCAG | CGGTTTATTG | ATCTATTGTT | AGACTTTATG | 1260 |
| GTAAAGAATC | CTCATTTATT | TGTTAATGGT | ACAGAGGATG | AAAGTAATAA | TGTTGTTACA | 1320 |
| AAATGTAATA | GTGATATTAA | AGAGGTTGCG | GAGTCATATT | TAACTCTTTT | ATAGTGAGAG | 1380 |
| GGTTAAAACT | AATTAATATG | TATTAAGGCC | CAATGTTGGA | ATTATTGTAT | TTCACTAGGC | 1440 |
| AACCTACTTA | CTAAAAGTAA | GATTATCCAT | TAGTGGATGT | TATAATATTG | GGTTTTTAA | 1500 |
| CACAATAATC | ATCGCCTTTC | GGTGTCGTTT | GATAGAAAAG | TAACCATTAG | CGATGAAAAA | 1560 |
| GTCAATATAA | AAAGCCATCC | GTAAAAAACG | GATGGCTTAC | CGTACATAGG | ATCGTTGGTA | 1620 |
| GGGCGGCGTA | TCCTACATCT | CTGGTAACTT | ACCTAGCCAA | TCAAATGCTT | GAGAACGGCG | 1680 |
| GTTAGATAAG | CGCGTGGGGA | ACCTTTCCCA | CCTCAAAGAT | CCTATATCAT | TATTATGTTA | 1740 |
| CTTTCTACAG | GTAGTATACC | ATGTTCTTAT | ATTTTAGTAA | ACTCCCCGTT | AGCTTAACAG | 1800 |
| GTCTTTGTAA | GCAATTAAAC | GTCCACTATT | CAATCGTCTT | TGGATTTTCG | CAGGACCGTT | 1860 |
| TTTTAGATCG | AACATAGTTG | ATAAGAACAA | ATAACCGCTT | GGGTCCAACT | TTATAGCAAT | 1920 |
| TAGTATATGG | TCATTTAAAA | TCTTTACCAA | TTCAACGCTA | TTAGGTTCTT | TAGGATTTTG | 1980 |
| CCCGACATAG | TCGGGGTGTT | CAACGATATC | TTTTATGTGC | GATGAATATT | TTTCATAAAT | 2040 |
| ACCAGGATGT | TGTTTCTTTA | CGTGCTTTAT | AAATGGGAAA | CATTTTTACA | TCGTTAGAAG | 2100 |
| TGCAAGTCAA | GTTATATGTA | TCTATAATGA | TTTGTGGAAG | TTTGCCACA | ACAGTTGGTT | 2160 |
| TATTTACAAT | CTTTTTTTA | TTAGCCGTCA | AATTTCTCCC | TCATCTCGTC | TCTTTATATC | 2220 |
| TTTATTTTAT | CATAAAGGAG | TATTTGAACC | GTCGCGCGGG | ACAGGTTTAT | GATAGGGATA | 2280 |

-continued

| | | | | | | |
|---|---|---|---|---|---|---|
| TTTTATTGAA | TAATTGATGG | TATAAGGGAC | TTTCATGCTT | GGAAAGTGGG | GATTATGAAT | 2340 |
| TAGATGCTTG | TCCACAATAT | GTTCCAATGT | AATTAAAATT | TATGTTCCCA | CCTTGACCAA | 2400 |
| ACATCACGTC | CATACTTAAA | TCGTCCCTCC | TTTAATAGGT | AAAATATTAA | TTTACCTTAA | 2460 |
| TAAAAAAATA | ATGGATAATA | GTATTCGTCT | GAATTTATAT | AATCAGGGGG | AACTATTGAT | 2520 |
| GCTGGGGATA | CTATTTACAG | CGGCGCCATC | TACTGATGTC | GTAAAGGATT | TGCAAGATAA | 2580 |
| AGTTATATCA | TTGCAGGATC | ATGAGGTAGC | GTTTTGAAC | ACCACGATAT | CTAATATGTT | 2640 |
| AACAGCAGTA | GGTATTGGAG | TGGCAATTAT | AACGGCGGTT | TTTACAGCAG | CGTTTGCTTA | 2700 |
| TGTTACATAT | TCTAATAAGC | GTGCTAAAAA | GAATATGGAC | GAGGCTAGTA | GAAAATTAGA | 2760 |
| AGAAGCAGAA | AGTAAAGTTT | CTGTGCTAGA | GGAGAAAAGC | GCTCAATTGG | AGAGGAAGAT | 2820 |
| TCTTGAAGCT | GAACAACTCT | TAGCTGATGC | CAATTCTATT | TCTAATGTGG | | 2870 |